United States Patent
Morimoto et al.

(10) Patent No.: US 9,857,296 B2
(45) Date of Patent: Jan. 2, 2018

(54) OPTICAL GRAIN EVALUATION DEVICE AND COMBINE HARVESTER PROVIDED WITH OPTICAL GRAIN EVALUATION DEVICE

(71) Applicant: Kubota Corporation, Osaka-shi (JP)

(72) Inventors: Susumu Morimoto, Yao (JP); Masao Soe, Yao (JP)

(73) Assignee: Kubota Corporation, Osaka (JP)

( * ) Notice: Subject to any disclaimer, the term of this patent is extended or adjusted under 35 U.S.C. 154(b) by 0 days.

(21) Appl. No.: 15/312,320

(22) PCT Filed: Aug. 14, 2015

(86) PCT No.: PCT/JP2015/072965
§ 371 (c)(1),
(2) Date: Nov. 18, 2016

(87) PCT Pub. No.: WO2016/059865
PCT Pub. Date: Apr. 21, 2016

(65) Prior Publication Data
US 2017/0115211 A1    Apr. 27, 2017

(30) Foreign Application Priority Data
Oct. 15, 2014   (JP) .................................. 2014-210874

(51) Int. Cl.
*G01J 5/02*       (2006.01)
*G01N 21/3554*   (2014.01)
(Continued)

(52) U.S. Cl.
CPC ..... *G01N 21/3554* (2013.01); *A01D 41/1277* (2013.01); *G01N 21/3563* (2013.01); *G01N 33/10* (2013.01)

(58) Field of Classification Search
CPC . G01N 21/3554; G01N 21/3563; G01N 33/10
(Continued)

(56) References Cited

U.S. PATENT DOCUMENTS 5,865,990 A * 2/1999 Novak ................. B07C 5/3425
                                                                209/579
6,424,416 B1   7/2002 Gross et al.
(Continued)

FOREIGN PATENT DOCUMENTS

JP    2103449 A   4/1990
JP    1019773 A   1/1998
(Continued)

*Primary Examiner* — David Porta
*Assistant Examiner* — Meenakshi Sahu
(74) *Attorney, Agent, or Firm* — The Webb Law Firm

(57) ABSTRACT

An optical grain evaluation device is provided with: a light-projecting part 58 through which light from a light source is projected to grain; a light-receiving part 59 on which light transmitted through the grain is incident; a grain evaluation unit 60 configured to evaluate the grain based on information relating to the received light; and a shielding part SH that separates an area between the light source 50 and the light-projecting part 59 from an area between the light-receiving part 59 and the grain evaluation unit 60, and prevents light from the light-projecting part 58 from directly entering the light-receiving part 59. The area between the light source 50 and the light-projecting part 58, and the area between the light-receiving part 59 and the grain evaluation unit 60 are configured, over the entirety of the areas, as air transmission areas in which light is transmitted through air.

10 Claims, 20 Drawing Sheets

(51) Int. Cl.
*A01D 41/127* (2006.01)
*G01N 21/3563* (2014.01)
*G01N 33/10* (2006.01)

(58) Field of Classification Search
USPC .................................................. 250/339.07
See application file for complete search history.

(56) References Cited

U.S. PATENT DOCUMENTS

| | | |
|---|---|---|
| 2001/0055116 A1 | 12/2001 | Maczura et al. |
| 2002/0039186 A1* | 4/2002 | Rosenberg ................ G01J 3/02 356/432 |
| 2004/0233675 A1* | 11/2004 | Meguro ............ G03B 21/2026 362/373 |
| 2005/0085283 A1 | 4/2005 | Kormann et al. |

FOREIGN PATENT DOCUMENTS

| | | |
|---|---|---|
| JP | 200121489 A | 1/2001 |
| JP | 2003513236 A | 4/2003 |
| JP | 2005274184 A | 10/2005 |
| JP | 20112375 A | 1/2011 |
| JP | 2013118857 A | 6/2013 |
| WO | 0131304 A1 | 5/2001 |

* cited by examiner

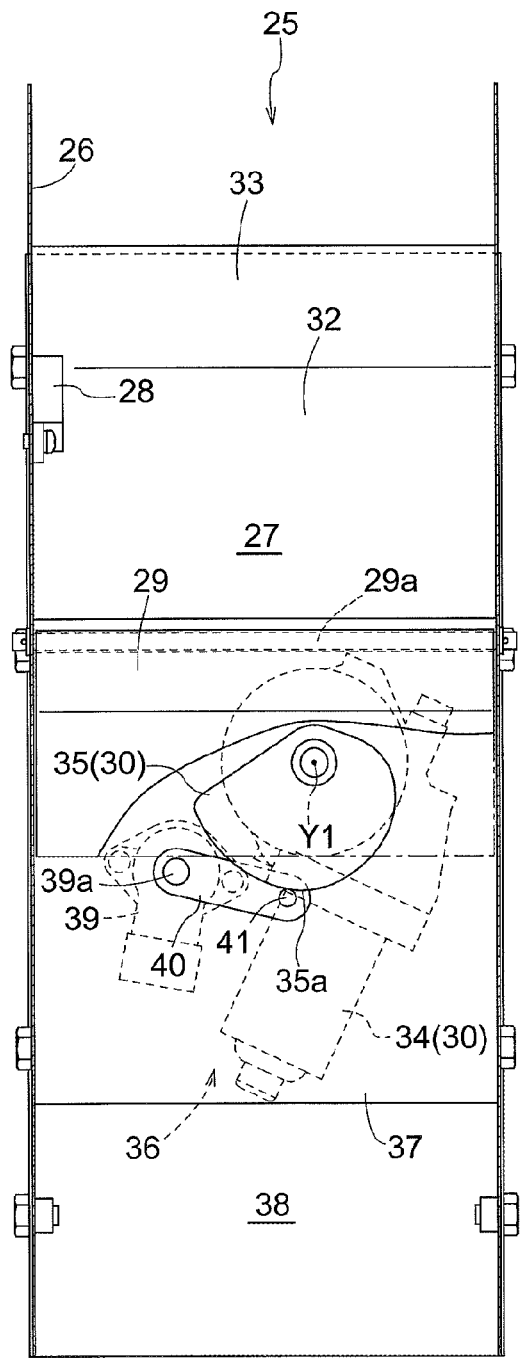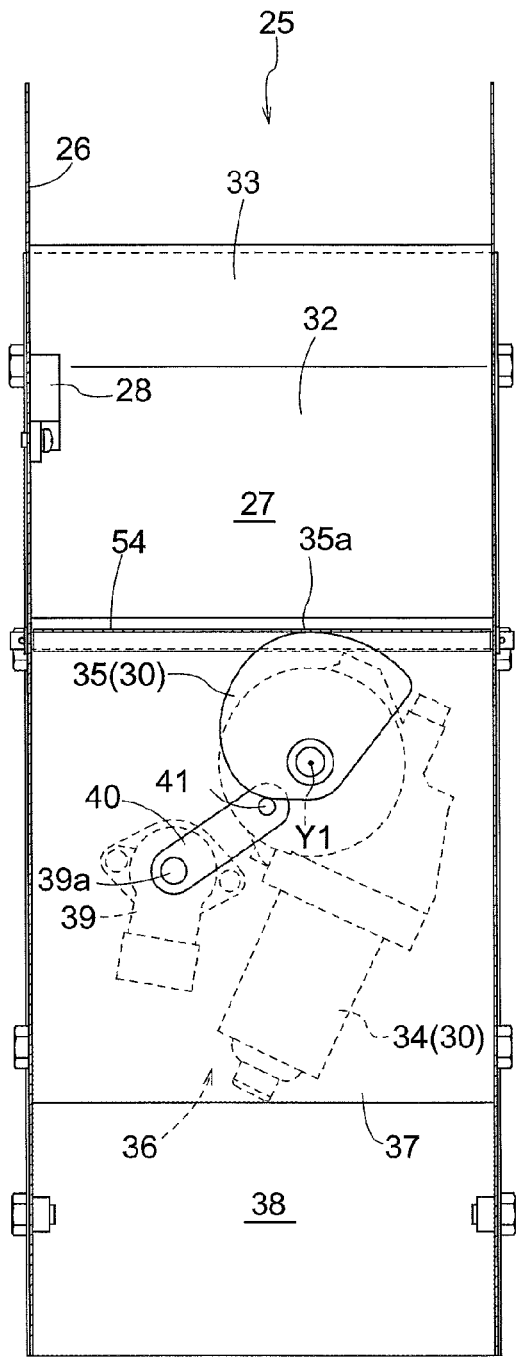

OPTICAL GRAIN EVALUATION DEVICE AND COMBINE HARVESTER PROVIDED WITH OPTICAL GRAIN EVALUATION DEVICE

CROSS-REFERENCE TO RELATED APPLICATIONS

This application is the United States national phase of International Application No. PCT/JP2015/072965 filed Aug. 14, 2015, and claims priority to Japanese Patent Application No. 2014-210874 filed Oct. 15, 2014, the disclosures of which are hereby incorporated in their entirety by reference.

TECHNICAL FIELD OF THE INVENTION

The present invention relates to an optical grain evaluation device that evaluates components contained in grains such as those of rice and wheat using optical measurement, and to a combine harvester provided with such an optical grain evaluation device.

BACKGROUND OF THE INVENTION

A device that uses diffuse reflectance characteristics of near-infrared light to measure the moisture content, protein and the like that are contained in flowing grain is known from Patent Literature 1. In this device, a light source that is arranged along a discharge duct of a farm machine such as a harvester, and is configured to irradiate the flow of cereal grain flowing in the discharge duct, and a detector that is configured to detect light that is scattered and reflected from the cereal grain are disposed in the same housing, and a shielding object is provided at a position at which it separates the detector from the light source that is lined up therewith. In this device, the detector receives light that is projected from the light source to the grain and is returned, but, due to the structural feature thereof, light from the light source is likely to directly enter the detector at the time of measuring the grain.

An optical internal-quality measuring means that evaluates the internal quality of grain that has been threshed and is temporarily stored is known from Patent Literature 2. This optical internal-quality measuring means is provided on a grain tank of a combine harvester, and is configured to irradiate the grain with near-infrared light, analyze an absorption spectrum based on spectroscopic analysis of the transmitted light, and determine the amounts of components such as moisture content, protein, and amylose that are contained in the grains based on a result of the analysis. The optical internal-quality measuring means is provided with: a light source; a measurement probe that guides a measurement light beam from the light source and diffusely-reflected light from the grain; a light-projecting/receiving adapter that irradiates the grain with the measurement light beam guided by the measurement probe, and receives the diffusely-reflected light from the grain to guide the received light to the measurement probe; a spectroscopic measurement unit that measures a spectroscopic spectrum of the diffusely-reflected light guided by the measurement probe; and an arithmetic unit that performs arithmetic processing on the components that are contained in the grains based on the spectroscopic spectrum obtained by the spectroscopic measurement unit. The light-projecting/receiving adapter and the measurement probe are housed in a cover body, and the light source, the spectroscopic measurement unit, and the arithmetic unit are housed in a separate device from the cover body. The measurement probe is constituted by a light-emitting optical fiber and a light-receiving optical fiber. The portions of the light-emitting optical fiber and the light-receiving optical fiber that respectively excludes an entrance end side, on which the measurement light beam is incident, of the light-emitting optical fiber, and an exit end side, from which the diffusely-reflected light exits, of the light-receiving optical fiber are formed coaxially such that the light-receiving optical fiber is located inside the ring-shaped light-emitting optical fiber. The light-projecting/receiving adapter is attached to the front end of the measurement probe, and is constituted by: an outer tubular body; an inner tubular body that is located inside the outer tubular body, and is coaxial with the outer tubular body while being distanced therefrom; and a connecting member that connects the outer tubular body and the inner tubular body.

This optical internal-quality measuring means has a configuration in which the light-emitting optical fiber is used to guide light from the light source to the light-projecting/receiving adapter, and the light-receiving optical fiber is used to guide light from the grain via the light-projecting/receiving adapter to the spectroscopic measurement unit. Furthermore, the light-projecting/receiving adapter is configured to include the outer tubular body and the inner tubular body that is coaxial with the outer tubular body while being distanced therefrom. This causes the problem of high manufacturing costs.

PRIOR ART DOCUMENTS

Patent Literatures

Patent Literature 1: US 2005/0085283 A
Patent Literature 2: JP 2013-118857 A

SUMMARY OF THE INVENTION

Problem(s) to be Solved by the Invention

In view of the above-described circumstances, desired is an optical grain evaluation device that mitigates the problem that light from a light-projecting part, which projects light from a light source to stored grain, directly enters a light-receiving part, on which light transmitted through the grain is incident, and suppresses the manufacturing costs for the light-projecting part and the light-receiving part.

Solution(s) to the Problem(s)

According to the present invention, an optical grain evaluation device includes, as feature configurations:

a light-projecting part through which light from the light source is projected to stored grain;

a light-receiving part on which light that has been projected to the grain through the light-projecting part and transmitted through the grain is incident, the light-receiving part being lined up with the light-projecting part at a distance;

a grain evaluation unit configured to evaluate the grain based on information relating to the light received by the light-receiving part; and a shielding part that separates an area between the light source and the light-projecting part from an area between the light-receiving part and the grain evaluation unit, so as to prevent light from the light-projecting part from directly entering the light-receiving part, wherein the area between the light source and the light-projecting part, and the area between the light-receiving part and the grain evaluation unit are entirely configured as air transmission areas in which light is transmitted through air.

According to the present invention, light from the light source is projected to stored grain through the light-projecting part, light transmitted through the grain enters the light-receiving part, and the grain evaluation unit can evaluate the grain based on information relating to the received light. By providing the shielding part, the area between the light source and the light-projecting part, and the area between the light-receiving part and the grain evaluation unit are separated from each other, and light from the light-projecting part is prevented from directly entering the light-receiving part.

Furthermore, since the area between the light source and the light-projecting part, and the area between the light-receiving part and the grain evaluation unit are configured, over the entirety of the areas, as air transmission areas in which light is transmitted through air, expensive optical fibers, measurement probes with a complex structures and the like are not necessary. Thus, it is possible to achieve a simple configuration and a low cost.

Accordingly, it is possible to provide an optical grain evaluation device that can mitigate the problem in which light from the light-projecting part, which projects light from the light source to stored grain, directly enters the light-receiving part, on which light transmitted through the grain is incident, and can suppress the manufacturing costs of the light-projecting part and the light-receiving part.

In the present invention, preferably, the light source and the light-projecting part are arranged linearly.

According to the present configuration, the light source and the light-projecting part are arranged linearly, and none of a reflecting mirror, a member that forms a bent light path and the like is present therebetween. As a result, a simpler configuration is achieved.

In the present invention, preferably, the optical grain evaluation device further includes a shutter that is switchable between an open state in which the light from the light source is allowed to pass through the light-projecting part, and a closed state in which the light is prevented from passing through the light-projecting part; and a correction mechanism configured to take in the light from the light source and obtain light information for correction for use in correcting an evaluation result regarding the grain when the shutter is in the closed state, wherein the shutter and the correction mechanism are provided as one piece.

According to the present configuration, in a non-measurement state, switching the shutter to the closed state can avoid a case where unnecessarily strong light is projected to the grain and the quality of the grain deteriorates. When the shutter is in the closed state, the correction mechanism operates to obtain light information for correction, and when the shutter is in the open state, the correction mechanism does not operate, and thus it is possible to appropriately perform measurement processing and correction processing.

In the present invention, preferably, the correction mechanism is provided with a correction optical filter through which the light from the light source passes to enter the grain evaluation unit.

According to the present configuration, the correction optical filter is used to measure, for example, a change in the light amount of light from the light source, or variations in wavelengths, so as to perform appropriate correction processing. Thus, it is possible to appropriately evaluate the grain.

In the present invention, preferably, the optical grain evaluation device further includes:

a light reflector configured to reflect the light from the light source and guide the light to the correction mechanism when the shutter is in the closed state.

According to the present configuration, it is possible to switch the shutter to the closed state, and to guide light from the light source to the correction mechanism by using the light reflector. Thus, with a simple configuration, it is possible to effectively use light from the light source as light for the correction mechanism.

In the present invention, preferably, the shutter is also used as the light reflector.

According to the present configuration, since the shutter is also used as the light reflector, it is possible to further simply the configuration.

In the present invention, preferably, the shutter and the correction mechanism are lined up on the same plane, and are provided so as to be movable together to switch between a state in which the shutter operates, and a state in which the correction mechanism operates.

According to the present configuration, since the shutter and the correction mechanism are lined up on the same plane, it is possible to use a simple operation of moving the shutter and the correction mechanism along the plane, to switch the state between the state in which the shutter operates, and the state in which the correction mechanism operates.

In the present invention, preferably, the shutter and the correction mechanism are provided integrally with a rotation body that rotates about an axis that is orthogonal to a mounting surface on which the light-projecting part and the light-receiving part are mounted, and the optical grain evaluation device is configured to be switched between a measurement state in which the shutter is in the open state, and a correction state in which the correction mechanism operates, by rotating the rotation body.

According to the present configuration, by rotating the rotation body, the optical grain evaluation device is switched between: the measurement state in which the shutter is in the open state, and the measurement processing is performed such that light is projected to the grain and light from the grain is received by the light-receiving part; and the correction state in which the correction mechanism operates, and the correction mechanism operates to obtain light information for correction. The operation state can be simply and smoothly changed with the operation to rotate the rotation body, compared to a configuration that employs a linear sliding operation, for example.

In the present invention, preferably, the optical grain evaluation device further includes:

a cooling fan configured to generate cooling air for cooling the light source; and a ventilation casing in which the light source and the cooling fan are arranged, and through which the cooling air is passed, wherein the ventilation casing is formed such that an air supply port for supplying the cooling air and an air discharge port for discharging the cooling air to the outside are located on the same plane.

According to the present configuration, since the ventilation casing is such that the air supply port and the air discharge port are located on the same plane, the configuration has advantages in which it is possible to arrange the air supply port and the air discharge port on one linear plane, and it is easy to install the ventilation casing in a box-shaped case or the like.

Furthermore, the present invention also relates to a combine harvester provided with the above-described optical grain evaluation device.

BRIEF DESCRIPTION OF THE DRAWINGS

FIG. 6A is a front view of an opening/closing operation mechanism in a state in which an opening/closing plate is operated to be located at a lowered open position, and FIG. 6B is a front view of the opening/closing operation mechanism in a state in which the opening/closing plate is operated to be located at a raised closed position.

DETAILED DESCRIPTION OF EMBODIMENTS

With reference to the drawings, an embodiment of an optical grain evaluation device according to the present invention will be described hereinafter, where grain harvested by a combine harvester is to be measured. In other words, in the embodiment, the optical grain evaluation device is installed in the combine harvester that harvests cereal grain.

Figure 1:
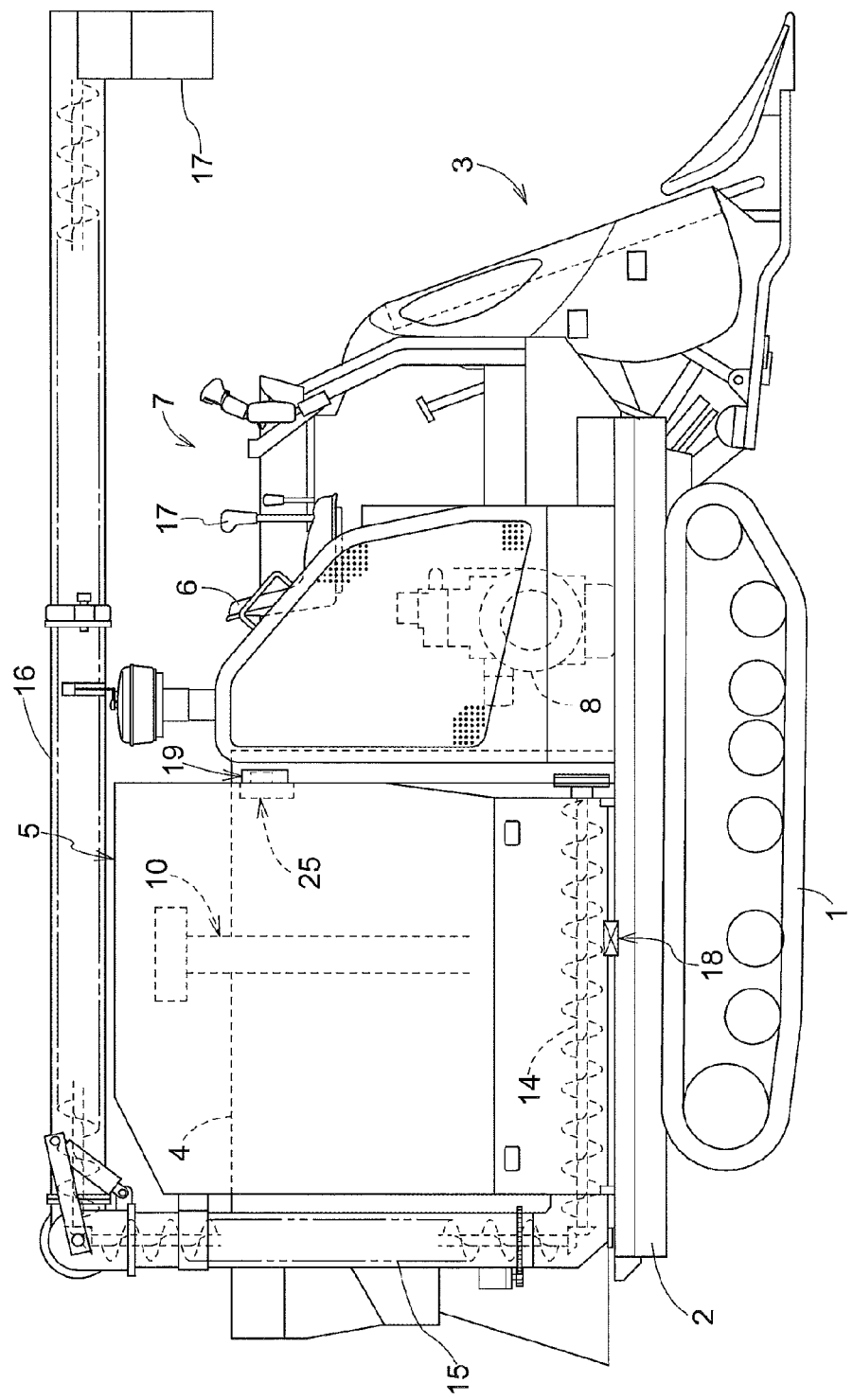
FIG. 1 is a side view illustrating the entirety of a combine harvester.
Figure 2:
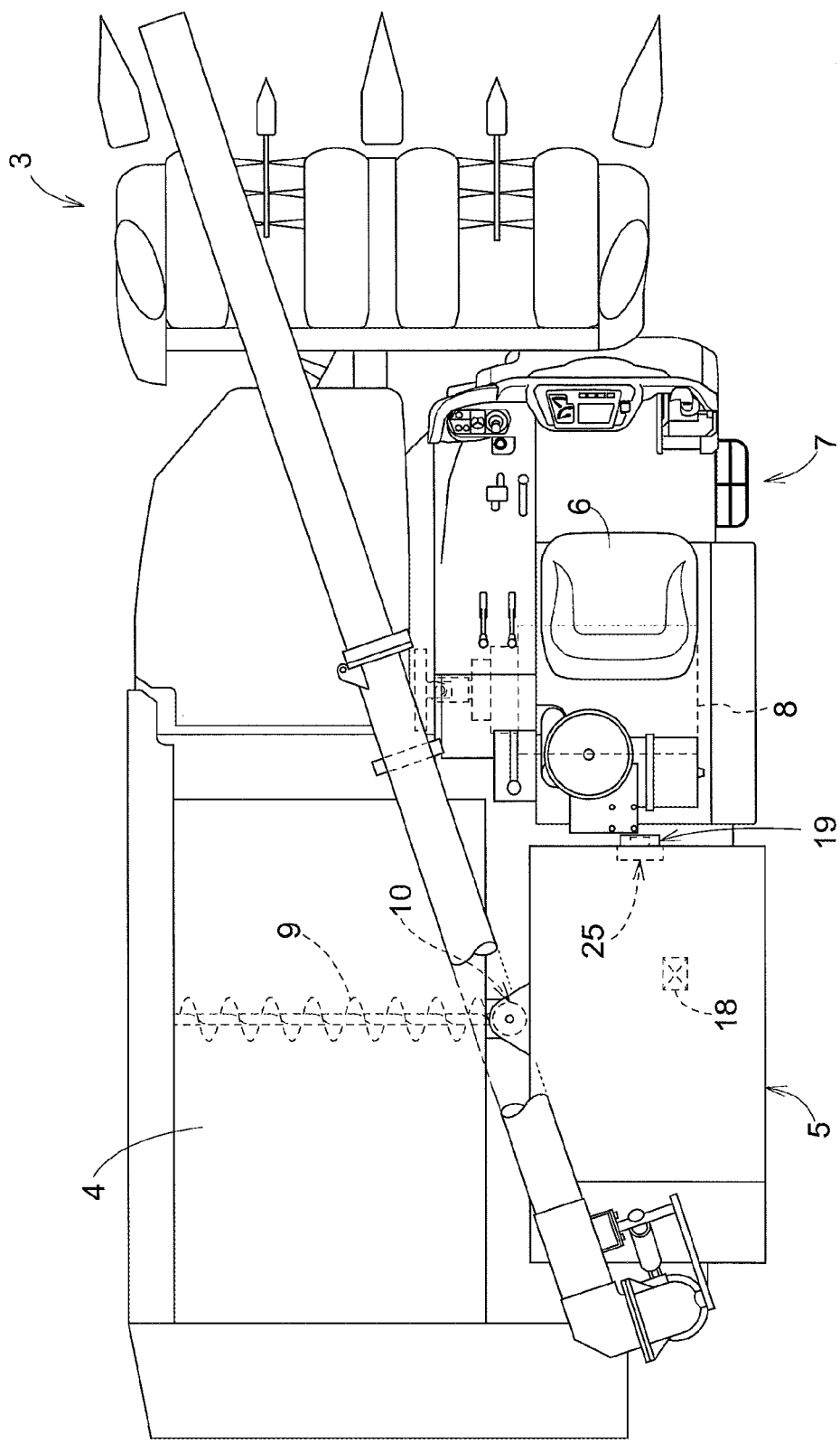
FIG. 2 is a plan view illustrating the entirety of the combine harvester.

FIG. 1 is a side view illustrating the entirety of a head-feeding type combine harvester in which an optical grain evaluation device is installed, and FIG. 2 is a plan view thereof. This combine harvester is configured to travel using a pair of right and left crawler traveling devices 1, and includes a machine body frame 2 whose front portion supports a reaper 3, and whose rear portion supports a threshing device 4 and a grain tank 5. Furthermore, an operation unit 7 including a driving seat 6 is provided on a lateral end side in the front portion of the travelling machine body, and an engine 8 is provided below the driving seat 6. The combine harvester is configured to perform a reaping operation while the machine body travels as a result of the power of the engine 8 being transmitted to respective units, but the power transmission system is not described in detail.

In the threshing device 4, the root side of reaped grain culms conveyed from the reaper 3 is held and conveyed to the rear side of the machine body by a feed chain (not shown) provided on the lateral left side, and the ear tip side of the grain culms is supplied to a threshing chamber (not shown) of a threshing unit and is threshed by a threshing drum (not shown) that is driven to rotate. In the threshing device 4, as a result of a sorting unit provided in the lower portion of the threshing chamber of the performing swinging sorting and wind sorting, threshing target objects are sorted into grain and dust such as that of straw waste, and the individual grains fall to the bottom portion inside the threshing machine body. The dust is discharged outward from the rear of the threshing machine body.

As shown in FIG. 2, a first screw conveyer 9 is provided in the bottom portion inside the threshing device 4. The individual grains are transversely conveyed toward the grain tank 5 by the first screw conveyer 9 in the transverse direction of the threshing machine body, are conveyed by a grain elevator device 10, and are stored in the grain tank 5.

The grain tank 5 will be described next.

Figure 3:
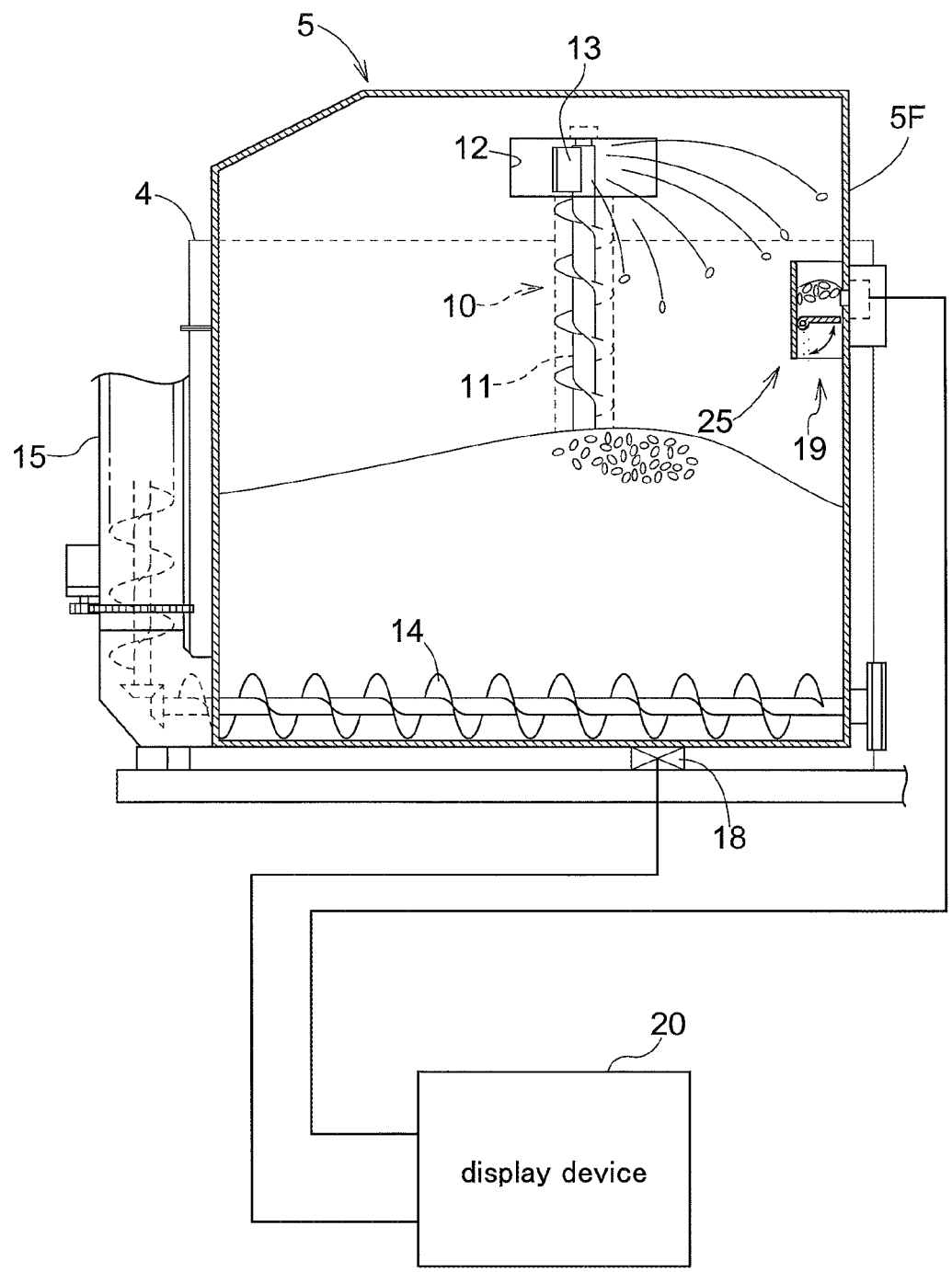
FIG. 3 is a side view in vertical section of a grain tank illustrating a state in which an optical grain evaluation device is installed.

The grain tank 5 is arranged on the lateral right side of the travelling machine body with respect to the threshing device 4 of the machine body frame 2, and arranged behind the engine 8. The grain elevator device 10 is arranged on the lateral left side of the grain tank 5. The conveyance terminal part of the grain elevator device 10 is connected to a lateral side part 5a of the grain tank 5. As shown in FIG. 3, the grain elevator device 10 is provided with an elevating/conveying screw 11 that is driven to rotate, and grain is elevated and conveyed by the elevating/conveying screw 11 to a spout 12 of the grain elevator device 10. A rotary vane 13 is provided at a position on the elevating/conveying screw 11 that opposes the spout 12, so as to be rotatable together with the elevating/conveying screw 11. The grain from the elevating/conveying screw 11 is scattered by the rotary vane 13 that is driven to rotate, and discharged from the spout 12 into a grain storage space 5b of the grain tank 5. Accordingly, grain from the threshing device 4 is sequentially stored in the grain storage space 5*b* of the grain tank 5.

As shown in FIGS. 1 and 3, the grain tank 5 is provided with, in the bottom portion thereof, a bottom screw 14 that is orientated in a front-rear direction of the travelling machine body. A vertical screw conveyor 15 that is orientated in a vertical direction of the travelling machine body is provided on the rear outside of the grain tank 5, and a horizontal screw conveyor 16 extends from the upper end portion of the vertical screw conveyor 15. The grain stored in the grain tank 5 is conveyed by the bottom screw 14, the vertical screw conveyor 15, and the horizontal screw conveyor 16, and is discharged from a spout tube 17.

As shown in FIG. 3, a load cell 18 is supported by the machine body frame 2 and arranged below the grain tank 5. The load cell 18 measures the weight of the grain stored in the grain tank 5. Furthermore, an optical grain evaluation device 19 is arranged on a front portion of the grain tank 5. The optical grain evaluation device 19 evaluates the internal quality of grain that is conveyed from the threshing device 4 and is loaded in the grain tank 5. The results of measurement by the load cell 18 and the optical grain evaluation device 19 are displayed on a display device 20 provided in the operation unit 7.

While described in details later, the optical grain evaluation device 19 has the shape of a rectangle that has a large height in the vertical direction and a small width in the right-left direction when viewed in the front-rear direction, and thus has, as a whole, the shape of a box that is narrow in the front-rear direction such that the width in the front-rear direction is smaller than the width in the right-left direction. This optical grain evaluation device 19 is provided on the operation unit 7 side of a front side wall 5F of the grain tank 5.

In other words, as shown in FIGS. 7 to 10, the optical grain evaluation device 19 is provided with, on the upper and lower sides thereof, coupling flange parts 24, and is coupled, using the coupling flange parts 24, to the front side wall 5F of the grain tank 5 with bolts. The front side wall 5F has an opening only at a position through which light for measurement is to pass, that is, the position being one into which a measuring head 31 that will be described later is inserted, and the optical grain evaluation device 19 is located on the operation unit 7 side of the front side wall 5F while being separated from the grain storage space 5*b* of the grain tank 5, and thus is provided on the outer side of the grain tank 5.

A sampling unit 25 that temporarily stores grain to be subjected to grain evaluation is provided at a position, behind the optical grain evaluation device 19, in the grain storage space 5*b* of the grain tank 5. The sampling unit 25 temporarily stores some of the grains loaded in the grain tank 5 as a target for measurement by the optical grain evaluation device 19, and when the measurement by the optical grain evaluation device 19 has ended, the stored grain is discharged into the grain storage space 5*b* of the grain tank 5.

Sampling Unit

The sampling unit 25 will be described next.

Figure 4:
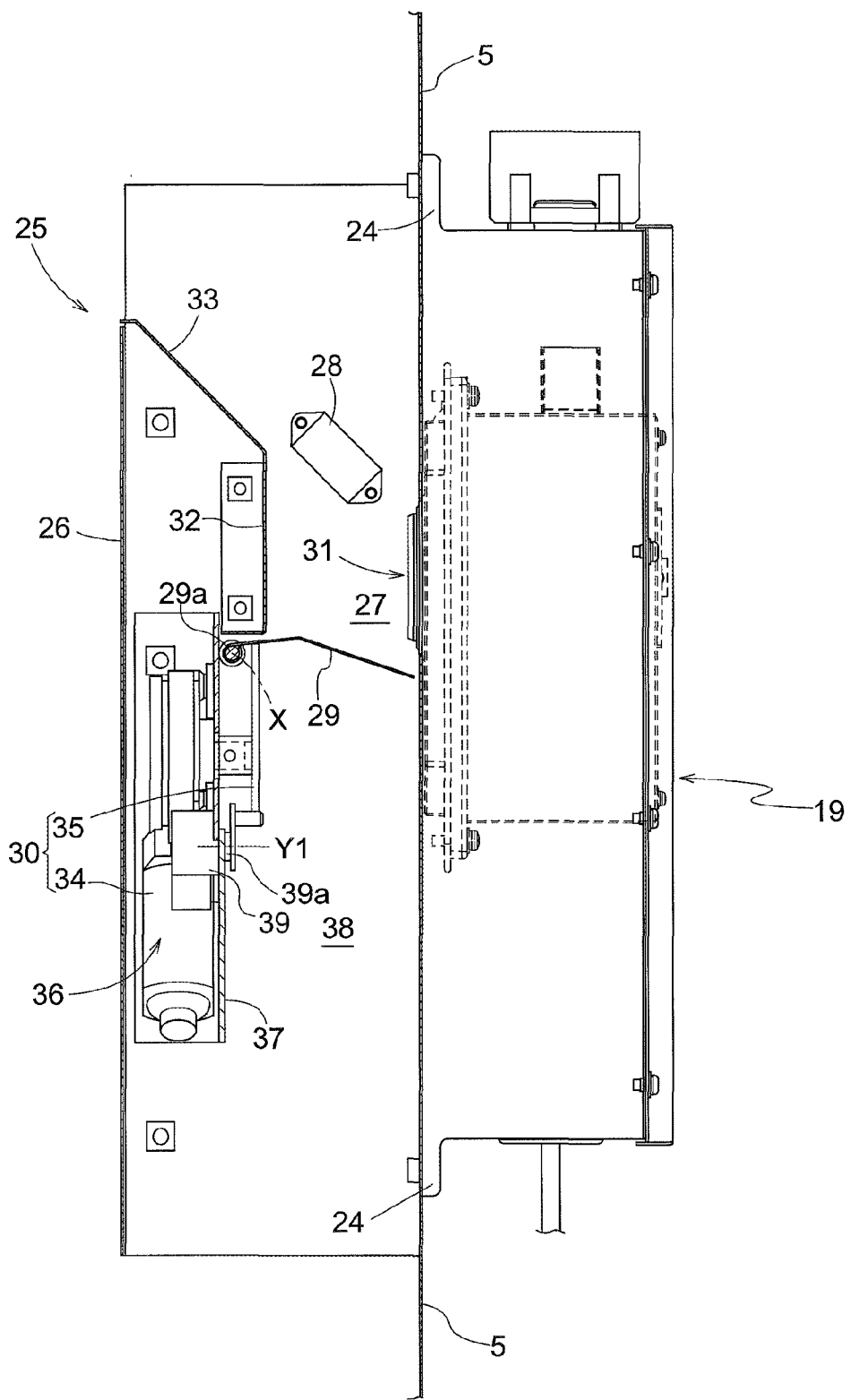
FIG. 4 is a side view in vertical section of a sampling unit and the optical grain evaluation device.

As shown in FIG. 4, the sampling unit 25 includes, in a holding part forming body 26 that is cylindrical and is orientated in the vertical direction of the grain tank 5, a receiving and holding part 27 that temporarily holds grain. The sampling unit 25 is further provided with: a full capacity sensor 28 that is arranged in an upper portion of the receiving and holding part 27; an opening/closing plate 29 that opens and closes the lower side of the receiving and holding part 27; and an opening/closing operation mechanism 30 that operates the opening/closing plate 29.

As shown in FIG. 4, an inclined guide surface 33 is provided above the receiving and holding part 27, at a position on a side that is opposite to the side of the receiving and holding part 27 on which the measuring head 31 of the optical grain evaluation device 19 is located. The inclined guide surface 33 is formed integrally with the upper portion of a wall plate 32, which forms one of the wall surfaces of the receiving and holding part 27. Grain that is present above the sampling unit 25 is guided, by the inclined guide surface 33, to flow downward to the receiving and holding part 27.

Figure 5:
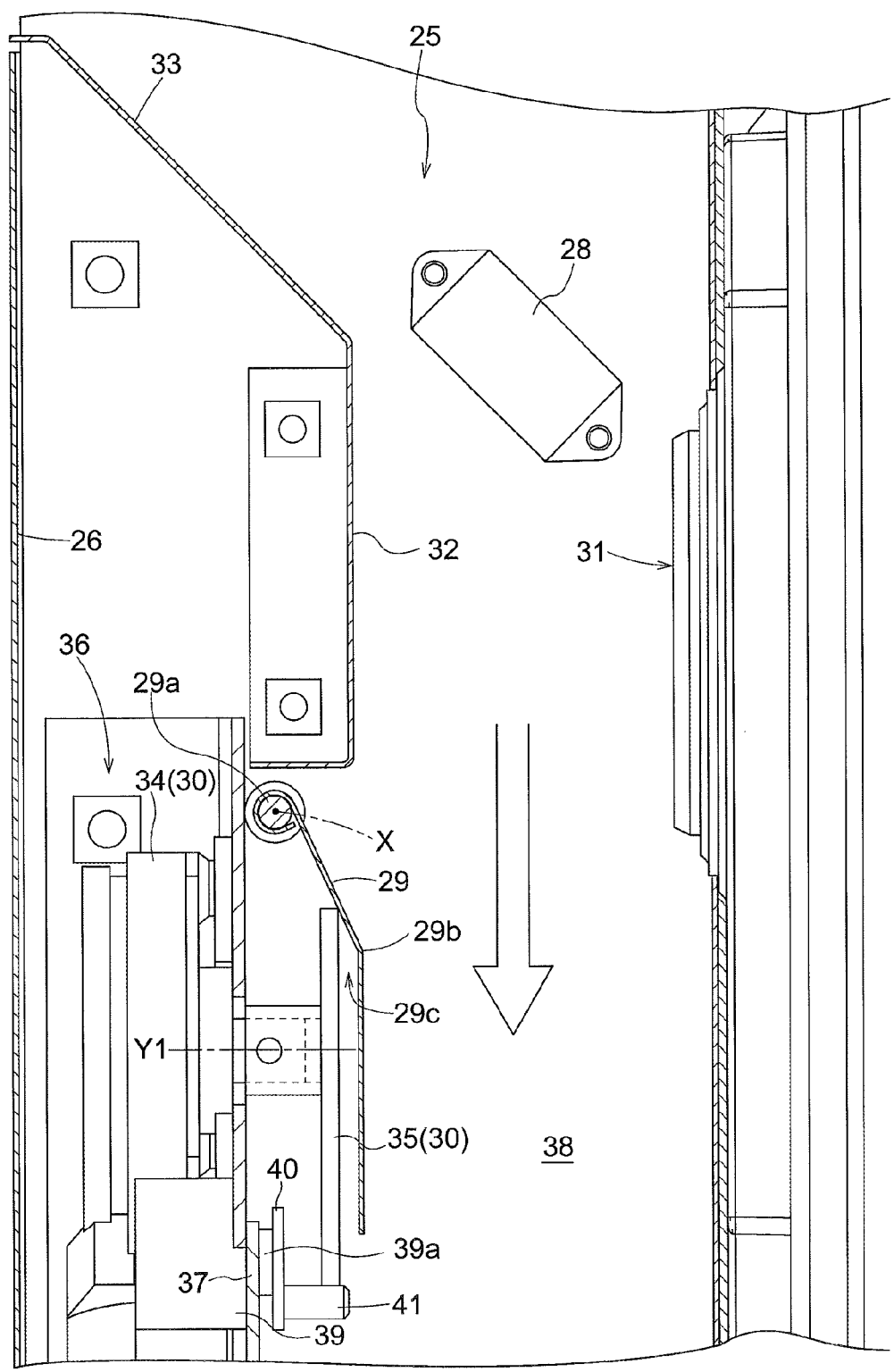
FIG. 5 is a side view in vertical section of the sampling unit.

As shown in FIGS. 4 and 5, the opening/closing operation mechanism 30 is provided with an electric motor 34 and a rotation cam 35 that is operated to rotate by the electric motor 34. The electric motor 34 and the rotation cam 35 are provided in the portion of the holding part forming body 26 that is located below the receiving and holding part 27. The electric motor 34 is housed in a motor room 36, which is formed by the holding part forming body 26 and a wall member 37 that is fixed to the inside of the holding part forming body 26. The rotation cam 35 is driven by the electric motor 34, and is operated to open and close the opening/closing plate 29. The opening/closing plate 29 is supported by the holding part forming body 26 so as to be able to swing about an opening/closing axis X of a supporting shaft 29*a*.

FIG. 4 is a side view illustrating the sampling unit 25 in a state in which the opening/closing plate 29 is closed. FIG. 6B is a front view illustrating the opening/closing operation mechanism 30 in a state in which the opening/closing plate 29 has been operated to be located at a raised closed position. As shown in FIGS. 4 and 6B, the rotation cam 35 is driven to rotate about a rotation axis Y1 in a closing operation direction, and is brought into a closing state when a large diameter part 35*a* is located above the rotation axis Y1. When the rotation cam 35 is brought into the closing state, the large diameter part 35*a* abuts against the portion, in the vicinity of the opening/closing axis X, on the bottom surface of the opening/closing plate 29, and acts to push up the opening/closing plate 29. Thus, the opening/closing plate 29 is located at the raised closed position.

FIG. 5 is a side view illustrating the sampling unit 25 in a state in which the opening/closing plate 29 is open. FIG. 6A is a front view illustrating the opening/closing operation mechanism 30 in a state in which the opening/closing plate 29 is operated to be located at a lowered open position. As shown in FIGS. 5 and 6A, the rotation cam 35 is driven to rotate about the rotation axis Y1 toward an opening operation side, and is brought into an opening state when the large diameter part 35*a* is located below the rotation axis Y1. When the rotation cam 35 is brought into the opening state, the action of the large diameter part 35*a* to push up the opening/closing plate 29 is cancelled. Thus, the opening/closing plate 29 is located at the lowered open position under its own weight.

When the opening/closing plate 29 is located at the lowered open position, the rotation cam 35 enters a recessed insertion part 29*c* that is formed on the rear side of the opening/closing plate 29 by a bent part 29*b*. Accordingly, the opening/closing plate 29 at the lowered open position is located at a position close to the located electric motor 34, so as to widen a falling passage 38.

A rotation potentiometer 39 is provided on a lateral side of the electric motor 34. As shown in FIGS. 4, 5, and 6, a detection arm 40 extends from a rotating operation shaft 39*a* of the rotation potentiometer 39 so as to be rotatable together therewith. The detection arm 40 is provided with a detection part 41 that comes into contact with and acts on the circumferential surface of the rotation cam 35. The rotation potentiometer 39 detects the opening/closing plate 29 at the raised closed position, and the opening/closing plate 29 at the lowered open position.

The full capacity sensor 28 is constituted by an electrostatic capacity type proximity sensor. The full capacity sensor 28 is arranged in the holding part forming body 26 so as to be orientated in a direction that intersects a direction in which light is projected from the measuring head 31 (the right-left direction of FIG. 4), when viewed in plan view.

The full capacity sensor 28 is attached to a surface of the holding part forming body 26 that faces to the receiving and holding part 27 while being inclined with respect to the vertical direction of the receiving and holding part 27. In other words, even if grain is located on the portion of the full capacity sensor 28 that protrudes from the surface of the holding part forming body 26, the grain falls by itself due to the slope of the full capacity sensor 28.

If the full capacity sensor 28 has detected a full capacity state in which the receiving and holding part 27 is full with grain, the optical grain evaluation device 19 measures the stored grain, and when the measurement of the optical grain evaluation device 19 is complete, the opening/closing plate 29 is controlled to move to the open position. Accordingly, the temporarily stored grain falls through the falling passage 38 into the grain storage space 5*b* of the grain tank 5.

If a set discharge time, which is set as a discharge time from a time at which the opening/closing plate 29 is opened to a time at which the measured grain needs to be discharged, has elapsed, and if no full capacity state is detected by the full capacity sensor 28, the opening/closing plate 29 of the opening/closing operation mechanism 30 is switched to the closed position. Accordingly, grain that has entered the receiving and holding part 27 is again stored as a measurement target.

Optical Grain Evaluation Device

The optical grain evaluation device 19 will be described.

The optical grain evaluation device 19 according to this embodiment measures internal quality by using a componential analysis method with spectroscopic analysis based on spectroscopic spectral data of near-infrared light, and is configured to project near-infrared light to grain, and measure an absorption spectrum based on spectroscopic analysis of the light transmitted therethrough. By evaluating the measurement result, the amounts of components such as moisture content, protein, and amylose that are contained in the grain are calculated. Furthermore, the optical grain evaluation device 19 can also determine the eating quality of the grain based on the calculation results of the amounts of the components such as moisture content, protein, and amylose.

Specific configurations thereof will be described hereinafter.

Figure 7:
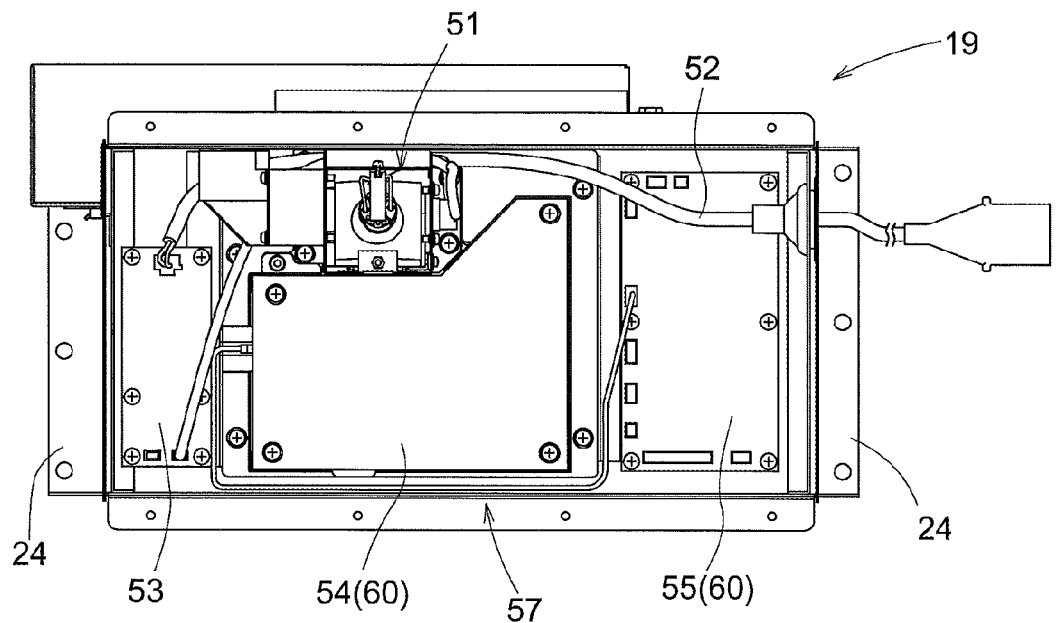
FIG. 7 is a front view of the optical grain evaluation device with a lid removed.

As shown in FIG. 7, the optical grain evaluation device 19 is provided with: a lamp unit 51 including a halogen lamp 50 with a reflector (light-collecting reflecting plate) that serves as a light source for projecting light for measurement into the receiving and holding part 27; a power supply unit 53 that adjusts electric power fed through a power supply code 52 and supplies the adjusted electric power to the halogen lamp 50; a spectroscopic measurement unit 54 that receives light projected to the grain and transmitted through the grain, and performs spectroscopic analysis on the received light; a control unit 55 that performs electrical control of the spectroscopic measurement unit 54, and various types of arithmetic processing for evaluating the internal quality of the grain based on detected information; a measuring head 31 that faces a measurement target (grain); and a box-shaped housing case 57 in which the constituent components are housed.

The measuring head 31 is provided with: a light-projecting part 58 through which light from the halogen lamp 50 is projected to the stored grain; and a light-receiving part 59 on which light transmitted through the grain is incident, and that is lined up with the light-projecting part 58 while being distanced therefrom. The measuring head 31 is exposed to the receiving and holding part 27 of the sampling unit 25 through the opening that is formed in the front side wall 5F of the grain tank 5, and is provided so as to face the stored grain.

The spectroscopic measurement unit 54 and the control unit 55 constitute a grain evaluation unit 60 that evaluates grain based on information relating to the light received by the light-receiving part 59.

Figure 9:
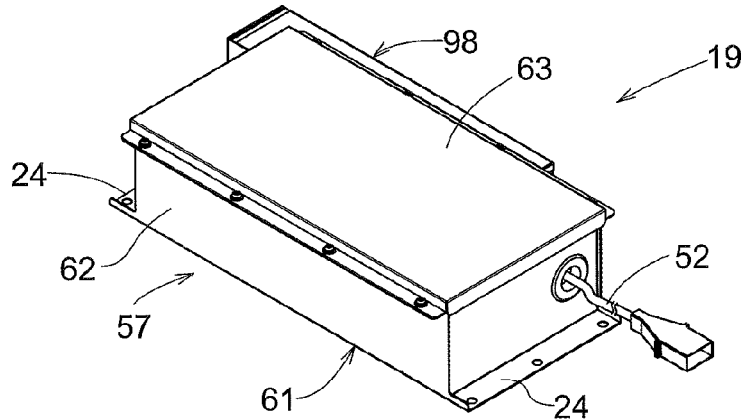
FIG. 9 is a perspective view of the optical grain evaluation device.
Figure 10:
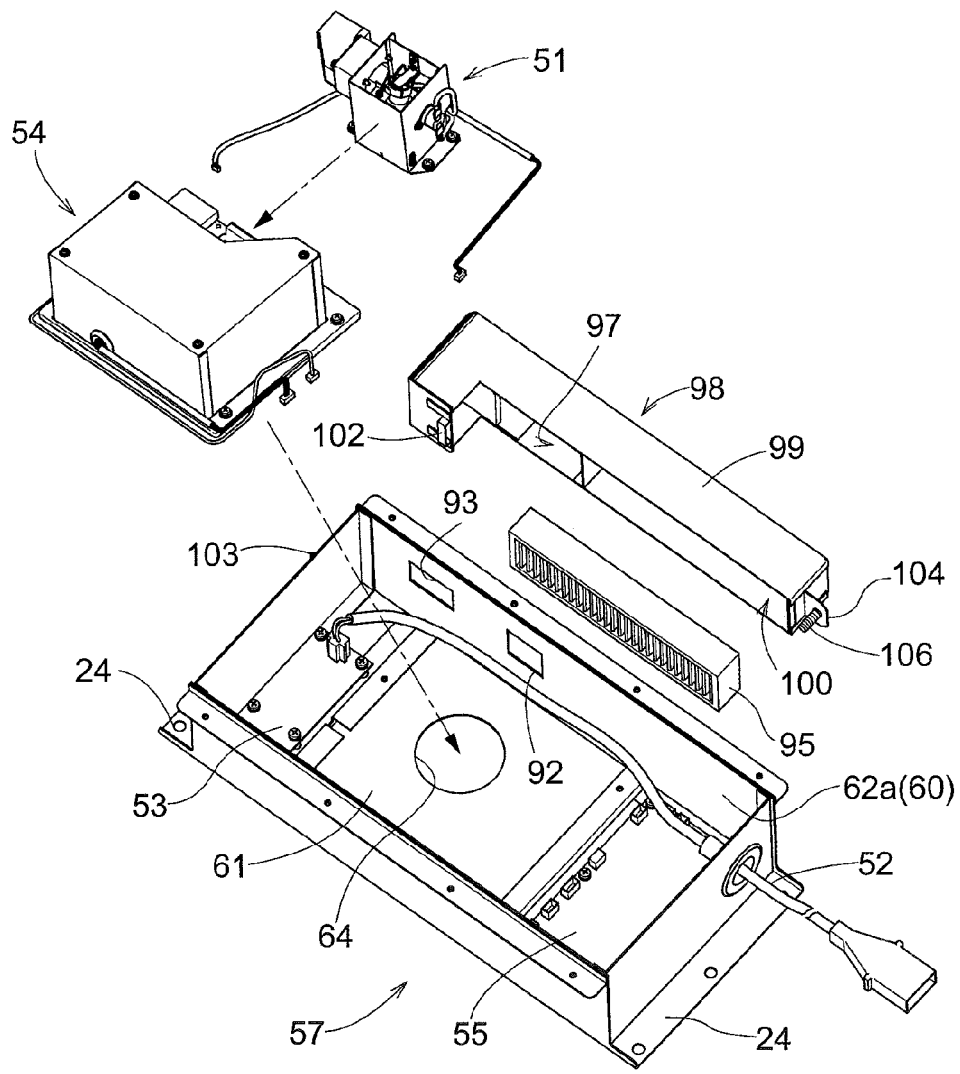
FIG. 10 is an exploded perspective view of the optical grain evaluation device.

As shown in FIGS. 9 and 10, the housing case 57 is provided with: a rectangular base wall 61 that serves as a bottom wall (bottom face), and is arranged adjacent to the wall body of the receiving and holding part 27; and a square-tubular peripheral wall 62 that is provided to stand upright from the peripheral edges of the base wall 61, and creates a housing space. Furthermore, as shown in FIG. 9, a lid 63 for covering the housing space that covers the opening formed by the peripheral wall 62 is provided while being fixed with bolts. The housing case 57 is configured to compactly house the constituent components.

As shown in FIG. 10, the base wall 61 is provided with a head mounting hole 64 that is a through hole for fixing the measuring head 31 so that it faces grain stored in the receiving and holding part 27. The measuring head 31 is inserted into this head mounting hole 64. In other words, the base wall 61 functions as a measurement wall that faces the stored grain. Furthermore, the lamp unit 51, the power supply unit 53, the spectroscopic measurement unit 54, and the control unit 55 are also fixed to the base wall 61 while being positioned with respect thereto.

Lamp Unit

The lamp unit 51 will be described next.

Figure 11:
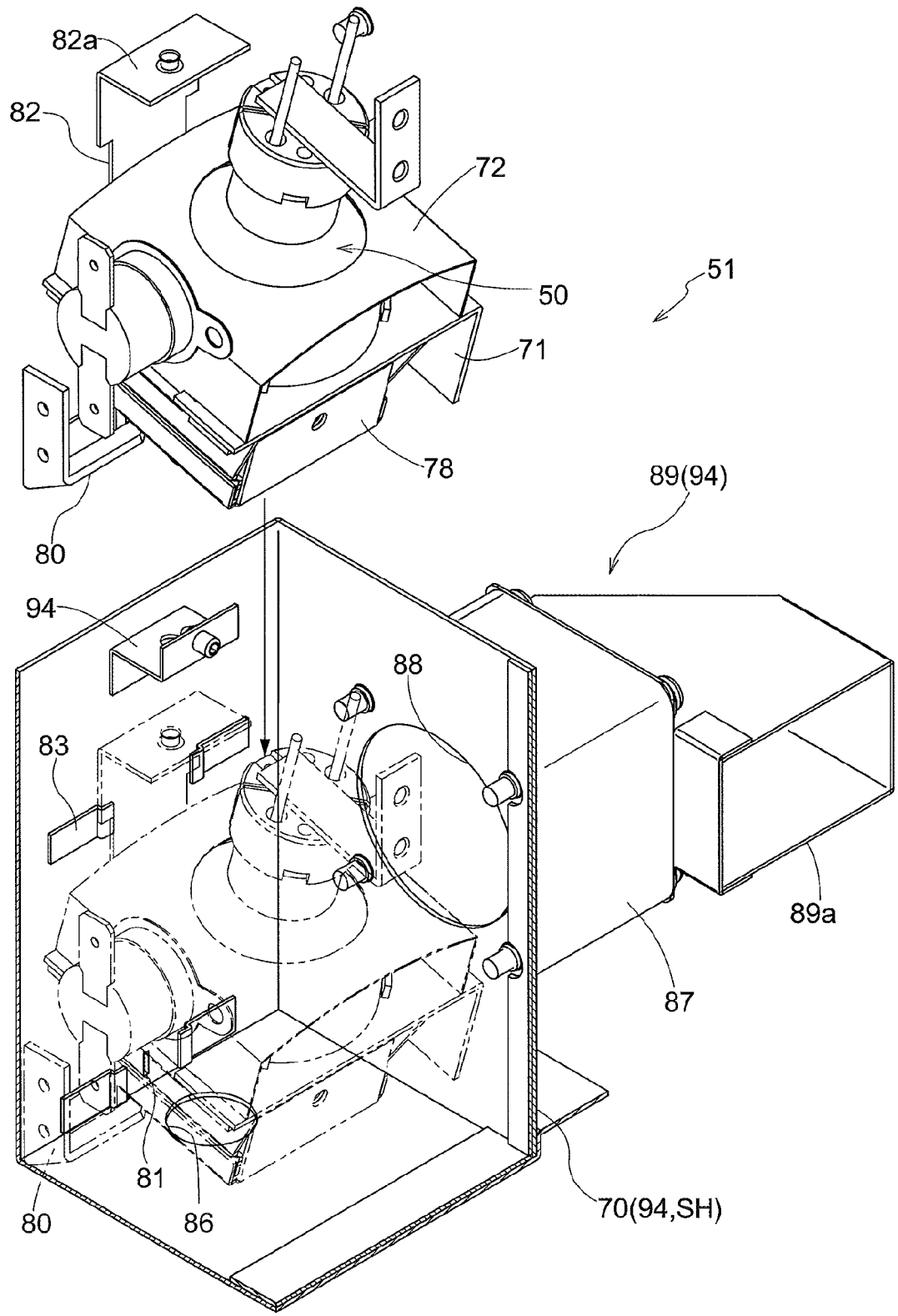
FIG. 11 is a perspective view of a lamp unit.
Figure 12:
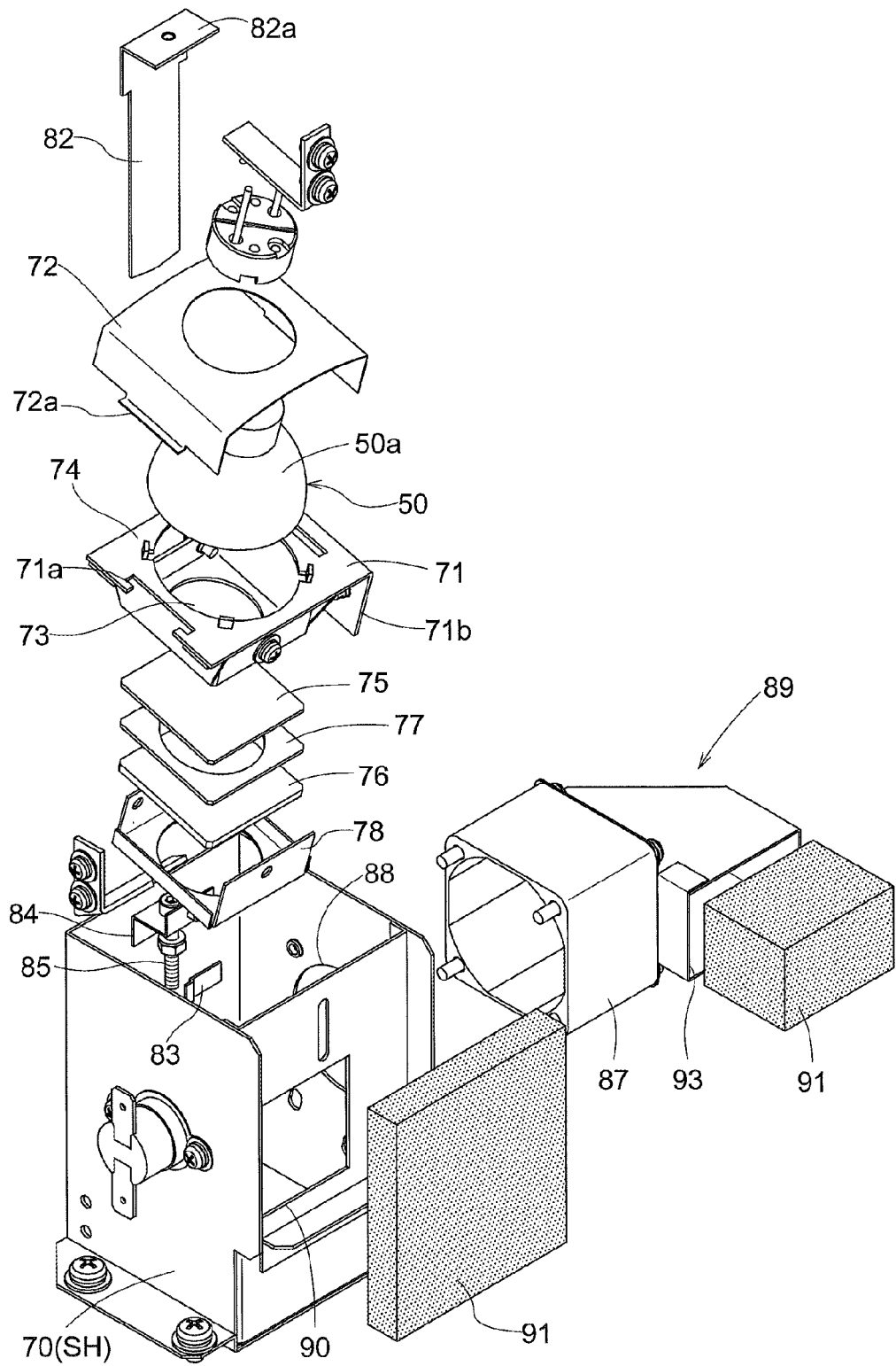
FIG. 12 is an exploded perspective view of the lamp unit.

As shown in FIGS. 11 and 12, in the lamp unit 51, the halogen lamp 50 with a reflector that serves as the light source is housed in a lamp housing 70 that is substantially box-shaped. This halogen lamp 50 is placed on a receiving base 71, and is held while being pressed by a pressing plate 72. The receiving base 71 has a light-passing opening 73 through which light from the halogen lamp 50 passes, and is provided with a mount holding part 74 in the circumference of the light-passing opening 73. A reflector 50*a* of the halogen lamp 50 is placed and supported in a state of abutting against the mount holding part 74. The pressing plate 72 prevents the halogen lamp 50 from moving upward, as a result of folded parts 72*a* on both right and left side ends of pressing plate 72 being engaged with engaging fixtures 71*a* formed in the receiving base 71 in a state in which the pressing plate 72 presses the halogen lamp 50. The receiving base 71 has an attachment part 71*b* on a lateral side of the mount holding part 74, and the attachment part 71*b* is fixed to the lamp housing 70.

There are provided: a heat-ray cut filter 75 that shields infrared rays of light projected from the halogen lamp 50 to make it difficult for heat to be transferred to the grain; a diffusing filter 76 that diffuses light so that the halogen lamp 50 projects light with a uniform light intensity; and a heat-resistant sealing member 77, at positions below the receiving base 71 in a light-projecting direction of the halogen lamp 50, while being held by a filter holder 78.

The lamp housing 70 is fixed to a rectangular support base 79 that supports the spectroscopic measurement unit 54, as will be described later. The measuring head 31 is provided on the support base 79, and the light-projecting part 58 of the measuring head 31 is irradiated with light projected from the halogen lamp 50 (see FIGS. 15A and 15B).

Figure 21:
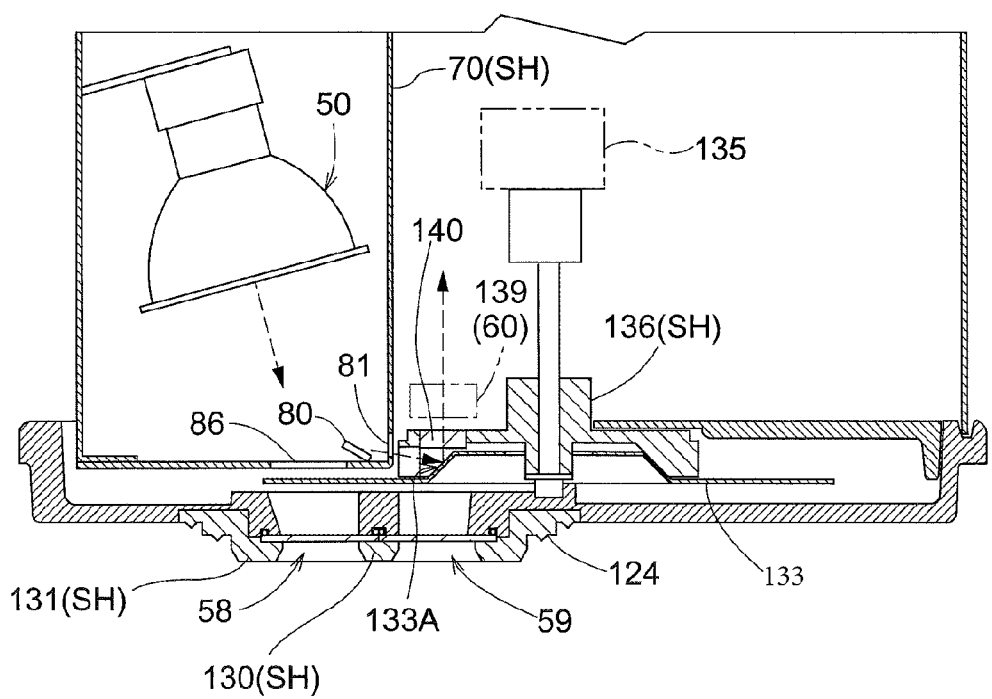
FIG. 21 is a plan view in transverse section of the main parts of the spectroscopic measurement unit performing the light amount correction processing.

Furthermore, part of the light projected from the halogen lamp 50 is used as information for correcting an evaluation result. In other words, as shown in FIGS. 11 and 21, a reflecting plate 80 that reflects part of the light projected from the halogen lamp 50 in a direction that is substantially orthogonal to the light-projecting direction, i.e., a direction toward the spectroscopic measurement unit 54 side, is provided at a position below the filter holder 78 in the light-projecting direction. Also, the side surface, on the spectroscopic measurement unit 54 side, of the lamp housing 70 is provided with a slit 81 (opening with a small width), and the light reflected by the reflecting plate 80 can be guided through this slit 81 toward the spectroscopic measurement unit 54.

As shown in FIG. 11, the reflecting plate 80 is provided and located at a lateral side end that is on the downward side in the light-projecting direction of the lamp housing 70. Furthermore, a light amount adjusting member 82 is provided that can change and adjust the light amount of light that is reflected by the reflecting plate 80 and is projected through the slit 81 so as to be subjected to correction. As shown in FIG. 11, the light amount adjusting member 82 is made of a band plate-shaped member that has, on one end thereof, a folded part 82a that is folded in an L-shape. A pair of right and left supporting members 83 are provided in the upper portion of the inner surface of the side surface, on the spectroscopic measurement unit 54 side, of the lamp housing 70, and a pair of right and left supporting members 83 are provided in the lower portion thereof. The light amount adjusting member 82 is supported by the supporting members 83 so as to be slidable.

The light amount adjusting member 82 is configured to change and adjust the open area, namely, the size of the opening, of the slit 81 by sliding and moving. As shown in FIG. 12, an adjustment screw 85 that can rotate relative to a fixed part 84 of the lamp housing 70 and is screwed to the folded part 82a of the light amount adjusting member 82 is provided. It is possible to change and adjust the size of the opening of the slit 81, by rotating the adjustment screw 85 to adjust the position of the light amount adjusting member 82 in a sliding direction.

Such an adjustment operation for adjusting the degree of opening of the slit 81 needs to be performed manually in advance before starting a harvesting operation.

Figure 18:
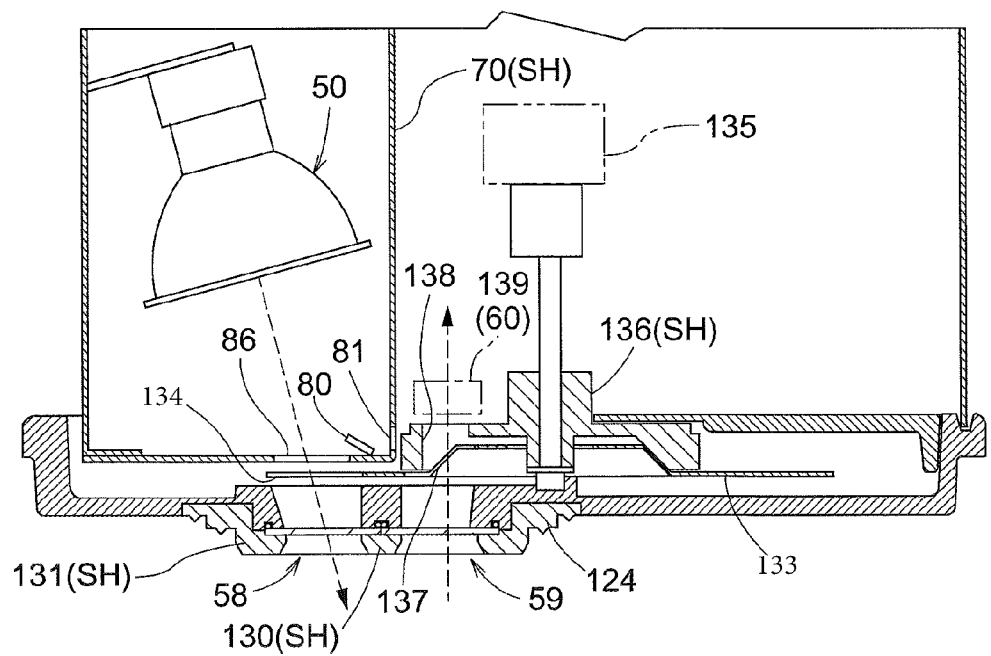
FIG. 18 is a plan view in transverse section of main parts of the spectroscopic measurement unit performing the measurement processing.

As shown in FIG. 18, the lamp housing 70 is provided with, on its side surface in the lower part in the light-projecting direction, a light-projecting opening 86 through which light from the halogen lamp 50 passes. The light-projecting opening 86 is located at a position that is displaced from the central position thereof toward the spectroscopic measurement unit 54 side. The halogen lamp 50 is supported while being slightly inclined in the longitudinal direction of the tubular lamp housing 70 so as to project light collected by the reflector 50a toward the light-projecting opening 86.

The lamp unit 51 is provided with a cooling fan 87 for taking in external air with a low temperature and discharging air with a high temperature to the outside, in order to suppress a rise in temperature of the lamp housing 70 that houses the halogen lamp 50 that becomes hot. In other words, as shown in FIGS. 11 and 12, the side surface of the lamp housing 70 that is adjacent to the side surface on the spectroscopic measurement unit 54 side is provided with a ventilation opening 88, and a discharge duct 89 for discharging air in the lamp housing 70 to the outside is provided on the outer side of this side surface. The cooling fan 87 is provided inside the discharge duct 89.

The side surface of the lamp housing 70 that faces the side surface on the spectroscopic measurement unit 54 side is provided with an external-air intake opening 90, and a dust removal filter 91 is provided on the outer side of this external-air intake opening 90. Another dust removal filter 91 is provided in the vicinity of an outlet 89a of the discharge duct 89.

As shown in FIG. 7, the lamp unit 51 is housed in the housing case 57.

In other words, the lamp unit 51 is arranged along the inner side of the one side wall 62a, in the longitudinal direction, of the peripheral wall 62 of the housing case 57. Also, as shown in FIG. 10, the one side wall 62a, in the longitudinal direction, of the housing case 57 is provided with an air inlet port 92 at the position that corresponds to the external-air intake opening 90, and an air discharge port 93 at the position that corresponds to the outlet 89a of the discharge duct 89.

As shown in FIG. 12, the external-air intake opening 90 and the outlet 89a of the discharge duct 89 are formed while being located on the same plane. As a result of the lamp unit 51 being arranged along the inner side of the side wall 62a of the housing case 57, the external-air intake opening 90 and the air inlet port 92 of the housing case 57 are in communication with and connected to each other, and the outlet 89a of the discharge duct 89 and the air discharge port 93 of the housing case 57 are in communication with and connected to each other.

Also, as a result of the cooling fan 87 performing a ventilation operation, external air is suctioned from the air inlet port 92 of the housing case 57, and air inside the lamp housing 70 is discharged from the air discharge port 93 through the discharge duct 89.

Accordingly, the lamp housing 70 and the discharge duct 89 constitute a ventilation casing 94 through which external air (cooling air) with a low temperature is passed. Also, the external-air intake opening 90 formed in the lamp housing 70 corresponds to an air supply port for supplying cooling air, and the outlet 89a of the discharge duct 89 corresponds to an air discharge port for discharging the cooling air to the outside.

Figure 8:
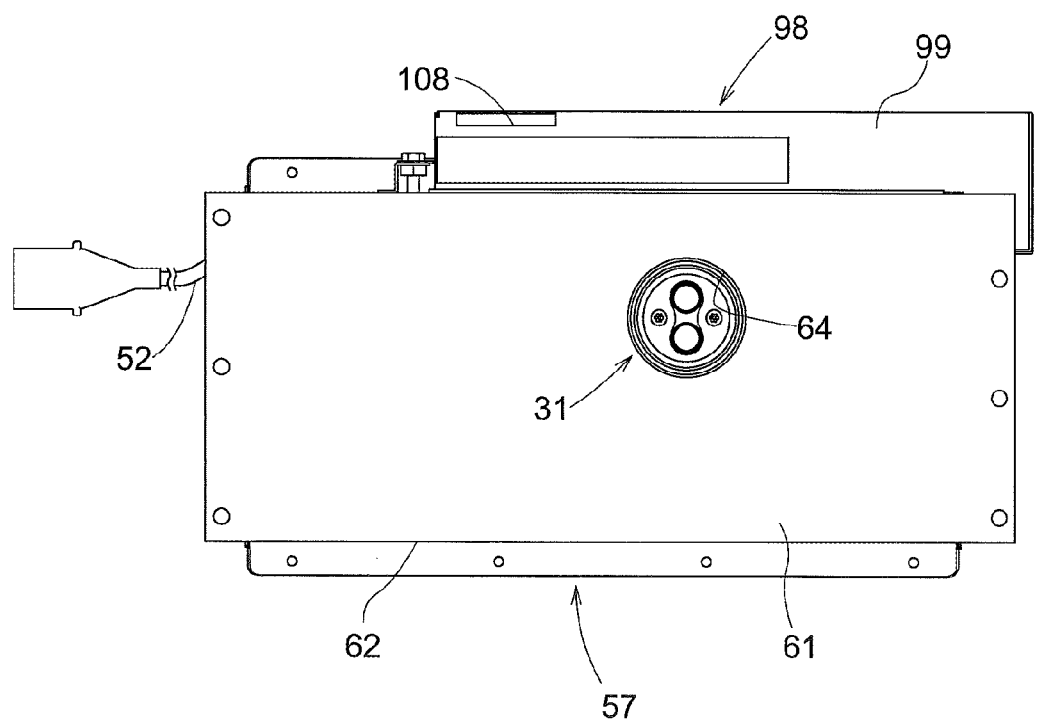
FIG. 8 is a rear view of the optical grain evaluation device.

As shown in FIGS. 8 and 10, the housing case 57 is provided with, on the outer side thereof, a ventilation unit 98. The ventilation unit 98 is provided with, inside thereof, a large-sized dust removal filter 95 so as to avoid being clogged up at an early stage when taking in external air containing a large amount of dust generated during a harvesting operation, and forms an exhaust air pathway 97 that covers the outside of the air discharge port 93 so as to prevent dust from entering the air discharge port 93.

Figure 22:
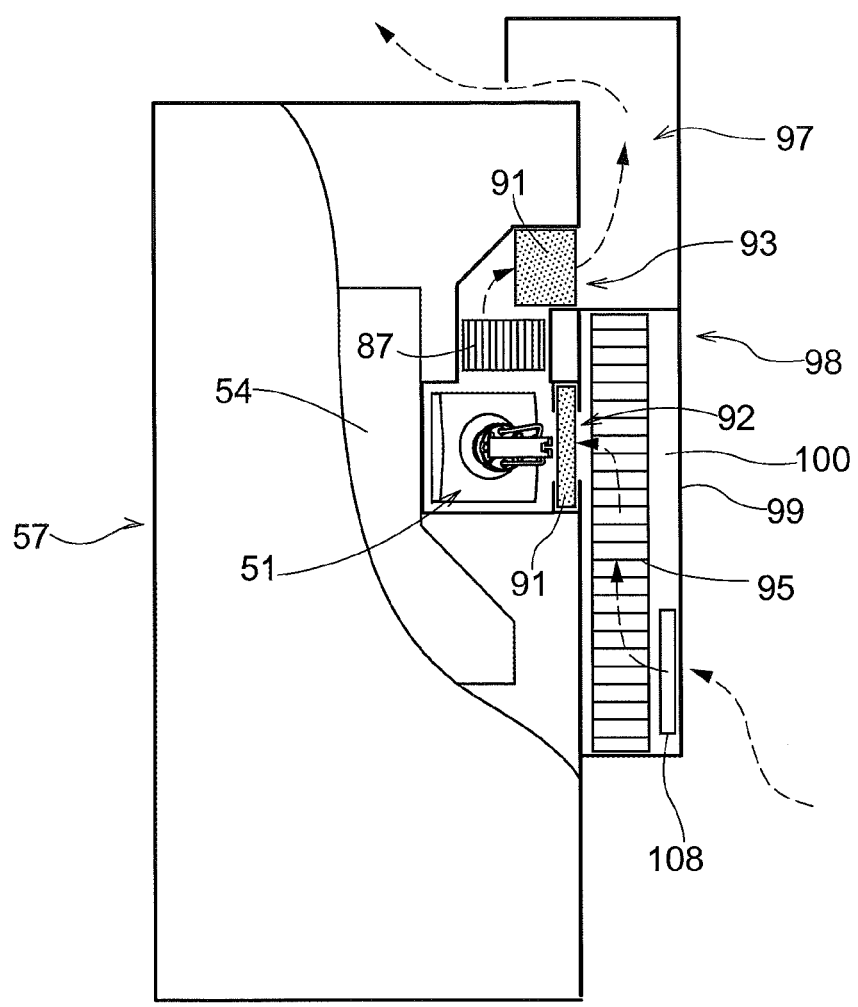
FIG. 22 is a view in section of a ventilation unit.

As shown in FIG. 22, the ventilation unit 98 is provided with: the elongated dust removal filter 95; and a ventilation pathway forming member 99 that houses the dust removal filter 95 and in which the bent-shaped exhaust air pathway 97 is formed. As shown in FIG. 10, the ventilation pathway forming member 99 substantially has the shape of a box whose one side surface is open and has a rectangular cross-section. A filter housing part 100 in which the dust removal filter 95 is housed is provided in the portion that extends linearly along the one side wall 62a, in the longitudinal direction, of the housing case 57. The bent-shaped exhaust air pathway 97 is formed in substantially an L-shape, such that it extends along the one side wall 62a in the longitudinal direction of the housing case 57 to an upper wall 62b that is continuous therewith. The filter housing part 100 and the exhaust air pathway 97 are partitioned by a block wall 101.

The ventilation pathway forming member 99 is fixed to and mounted on the housing case 57, as a result of a bracket 104 that is fixed to the lower end thereof being fixed to a bracket 105 of the housing case 57 with a single bolt 106 in a state in which an engaging fixture 102 formed at an end position of the exhaust air pathway 97 being engaged with an engaging fixture 103 of the housing case 57. Note that the ventilation pathway forming member 99 is provided with a sealing material 107 that is formed at a position over the entire periphery at which the ventilation pathway forming member 99 abuts against the housing case 57. With such a configuration, it is possible to easily remove the single bolt 106 to detach the ventilation pathway forming member 99, while preventing ventilation air from leaking. This makes it easy to perform a maintenance operation such as exchanging or cleaning of the dust removal filter 95.

When the ventilation pathway forming member 99 is mounted, the upper side portion of the filter housing part 100 is brought into communication with and connected to the air inlet port 92 of the housing case 57. As shown in FIG. 22, the filter housing part 100 has an air inlet port 108 at a corner on the lower side thereof. The filter housing part 100 includes, on the rear side thereof, a space for ventilation, and if part of the elongated dust removal filter 95 is clogged, it is possible to perform ventilation at a different position in the longitudinal direction, that is, at a non-clogged position. Thus, it is possible to prevent a problem in which the dust removal filter 95 is clogged in a short period of time.

Spectroscopic Measurement Unit

The spectroscopic measurement unit 54 will be described. As shown in FIGS. 13, 14, 15A, and 15B, the spectroscopic measurement unit 54 is provided with, for example: a rectangular support base 79 that supports the entire unit, and is fixed to the housing case 57 with bolts connected at a plurality positions; a spectroscopic analysis part 120 that receives light from grain to disperse the light, and measures the intensity of the light at each wavelength to measure the attenuation rate of the light at specific wavelengths; and a switching mechanism 121 that switches the spectroscopic measurement unit 54 between, for example, a state in which light is projected to grain, and measurement processing is performed based on the light from the grain, a state in which correction is performed based on information for correction, and a standby state in which no measurement or the like is performed.

Figure 15A:
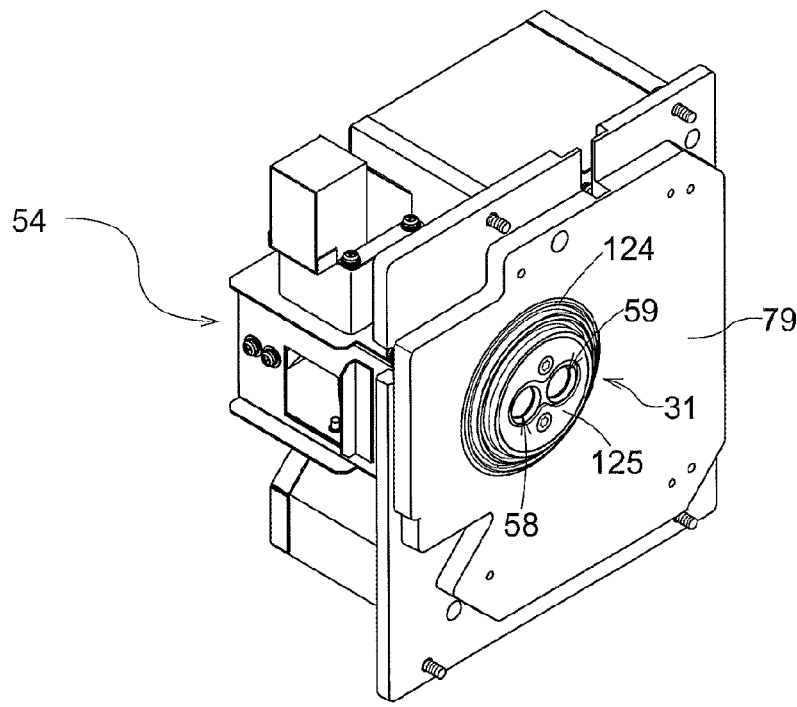
FIG. 15A is a perspective view of the spectroscopic measurement unit.
Figure 15B:
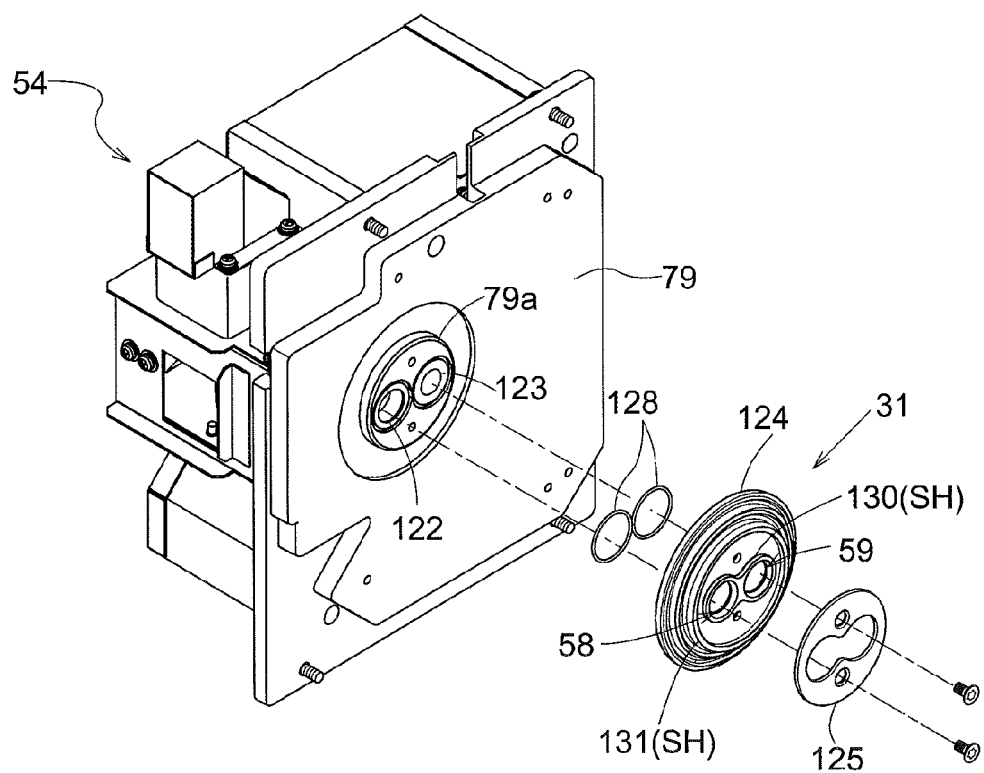
FIG. 15B is a perspective view of the spectroscopic measurement unit in a state in which a measuring head is exploded.
Figure 16:
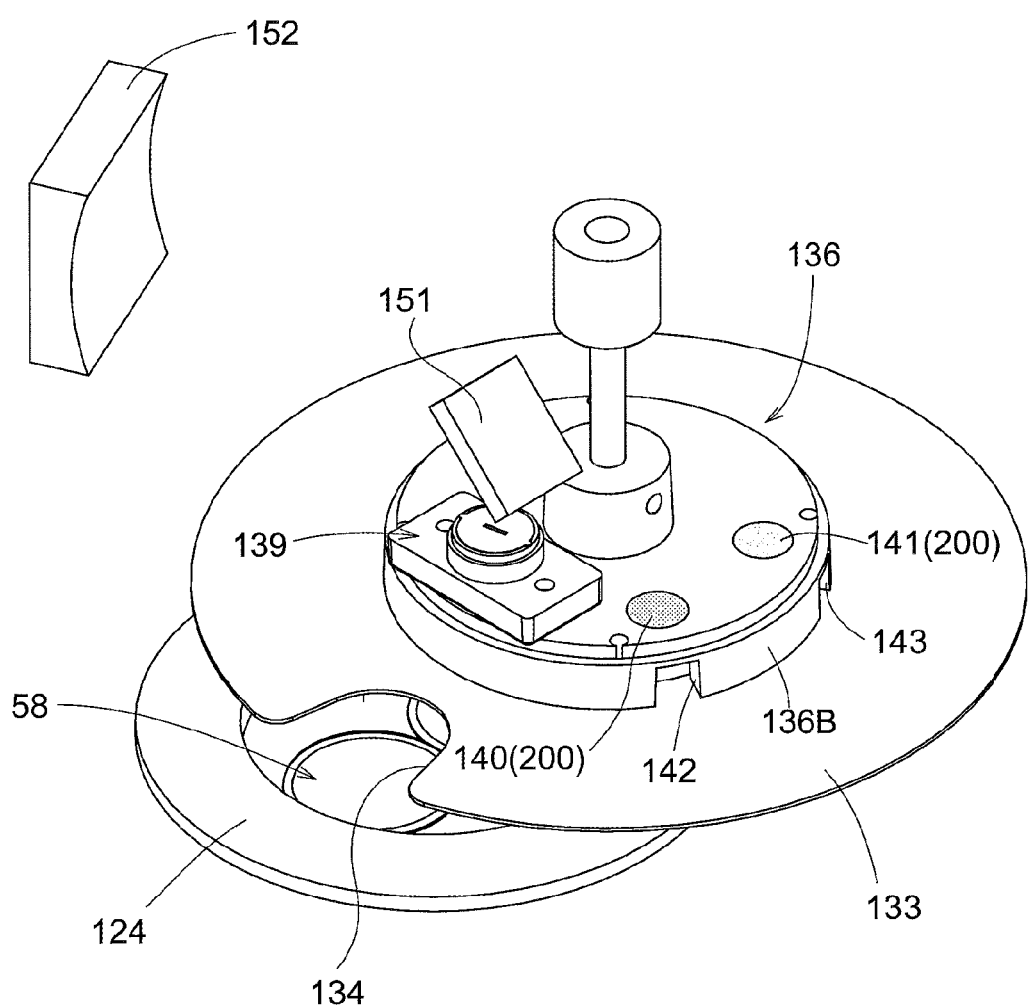
FIG. 16 is a perspective view of main parts of the spectroscopic measurement unit performing measurement processing.

The measuring head 31 is provided in a bottom part of the support base 79. In other words, as shown in FIGS. 15A and 15B, the bottom part of the support base 79 has a circular protruding part 79a that cylindrically protrudes outward, and is formed integrally therewith. The circular protruding part 79a is provided with: a light-projecting opening 122 through which light projected from the halogen lamp 50 passes toward grain; and a light-receiving opening 123 through which light from the grain passes toward the spectroscopic analysis part 120, the openings penetrating through the circular protruding part 79a. A cover member 124 whose cylindrical outer circumferential part is provided with a circular recess is externally fitted to the portion of the circular protruding part 79a that protrudes to the outside, and is fixed thereto with bolts while being pressed by a circular disk-shaped pressing plate 125 from the outside.

Figure 14:
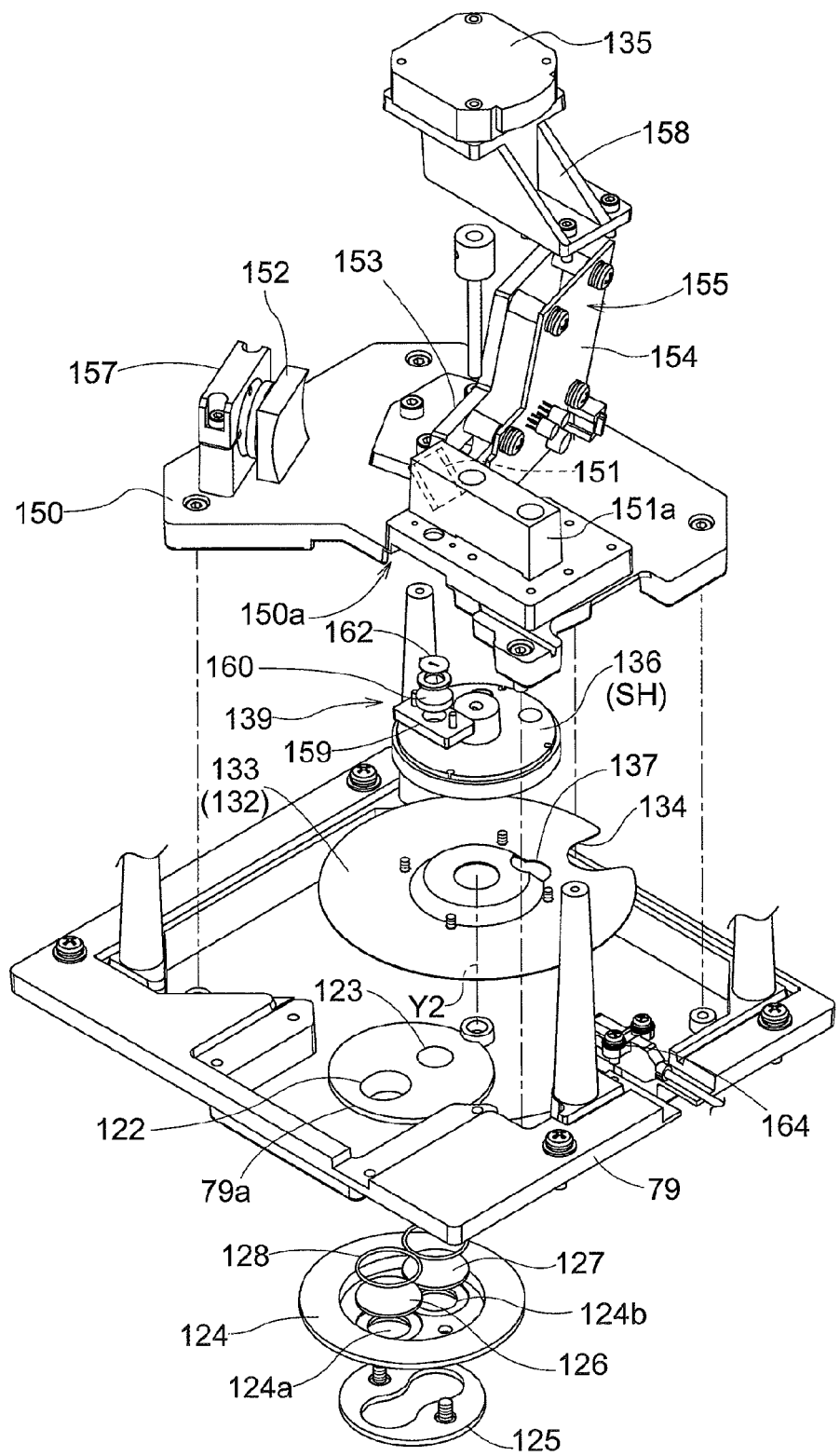
FIG. 14 is an exploded perspective view of the spectroscopic measurement unit.

As shown in FIG. 14, a circular light-projecting glass plate 126 and a circular light-receiving glass plate 127 are interposed between the cover member 124 and the circular protruding part 79a via O rings 128. Note that, in FIGS. 15A and 15B, the light-projecting glass plate 126 and the light-receiving glass plate 127 are attached to the cover member 124. The cover member 124 and the circular protruding part 79a respectively have, on their opposing surfaces, circular recessed insertion parts into which the light-projecting glass plate 126 and the circular light-receiving glass plate 127 are inserted, so that they can be interposed without being displaced. The light-projecting glass plate 126 and the light-receiving glass plate 127 are made of hard glass so as to serve as protection films because they are arranged in intimate contact with stored grain.

As shown in FIG. 18, the lamp housing 70 is fixed to an attachment part 129 that is provided in the vicinity of the circular protruding part 79a of the support base 79. The lamp housing 70 is mounted such that the light-projecting opening 86 formed in the side surface on the downside in the light-projecting direction is located at the position that corresponds to the circular protruding part 79a.

Accordingly, light that is emitted from the halogen lamp 50 is projected to grain stored in the receiving and holding part 27 through the light-projecting opening 122 and the light-projecting glass plate 126. In this way, the portion that projects light to the grain constitutes the light-projecting part 58. Furthermore, the light projected to the grain through the light-projecting part 58 and is transmitted through the grain enters the spectroscopic analysis part 120 through the light-receiving glass plate 127 and the light-receiving opening 123. In this way, the portion that receives light constitutes the light-receiving part 59. The measuring head 31 is thus configured by the circular protruding part 79a, the cover member 124, the light-projecting glass plate 126, the light-receiving glass plate 127, the O rings 128, the pressing plate 125, and the like.

The light-projecting part 58 and the light-receiving part 59 are lined up at a predetermined distance so as to make it easy for part of the light that is projected to grain through the light-projecting part 58 and is transmitted through the grain to enter the light-receiving part 59. This is because the principle of measurement of the optical grain evaluation device 19 uses the fact that the percentage of absorption (absorbance) of projected light from the light-projecting part 58 as a result of the light passing through the grain varies depending on the quality (such as moisture content) of the grain. Light that is projected and is transmitted through grain should enter the light-receiving part 59, but, at this time, it is necessary to avoid the light projected from the light-projecting part 58 from directly entering the light-receiving part 59. It is preferable that light projected from the light-projecting part 58 enter grain and the light transmitted through the grain enter the light-receiving part 59. Therefore, the light-projecting part 58 and the light-receiving part 59 are exposed to the outside so as to come into intimate contact with stored grain at the time of measurement. Furthermore, a protruding ridge 130 that protrudes to the outside (to the grain side) is provided between the light-projecting part 58 and the light-receiving part 59 so as to prevent light from the light-projecting part 58 from directly entering the light-receiving part 59. Furthermore, in order to prevent the entrance of light from the periphery, a shielding peripheral wall 131 that encloses the outer peripheries of the light-projecting part 58 and the light-receiving part 59 is provided.

In other words, the cover member 124 is provided with a first hole 124a and a second hole 124b such that the light-projecting glass plate 126 and the light-receiving glass plate 127 are exposed therethrough. The peripheral edge portions of the first hole 124a and the second hole 124b are raised in a shape of a frame for reading glasses, in order to generate the protruding ridge 130. Similarly, the peripheral region of the cover member 124 is also raised in the shape of a ring, and this ring-shaped raised portion functions as the shielding peripheral wall 131.

The circular protruding part 79a in the bottom part of the support base 79 is provided with, on the inner surface side thereof, a shutter 132 that can switch between an open state in which light from the halogen lamp 50 is allowed to pass through the light-projecting part 58, and a closed state in which the light is prevented from passing therethrough. This shutter 132 is configured by a circular disk body 133 that serves as a circular disk-shaped rotation body. As shown in FIGS. 14, and 16 to 18, the circular disk body 133 that is rotatable about an axis Y2 extending in a direction substantially orthogonal to the bottom part (that corresponds to a mounting surface on which the light-projecting part 58 and the light-receiving part 59 are mounted) of the support base 79 is provided. The circular disk body 133 is provided with a cut-out recess 134 that is formed by cutting out a part, in the circumferential direction, of the outer peripheral edge portion of the circular disk body 133. This circular disk body 133 is driven to rotate by a driving motor 135, and allows light from the halogen lamp 50 to pass through the light-projecting part 58 when the cut-out recess 134 is located at a measurement rotational position at which the cut-out recess 134 overlaps the light-projecting opening 122. In other words, the shutter 132 is in the open state. On the other hand, when the cut-out recess 134 is displaced from the light-projecting opening 122, the light-projecting opening 122 is shielded and light from the halogen lamp 50 is prevented from passing through the light-projecting part 58. In other words, the shutter 132 is in the closed state. The driving motor 135 is configured by a stepping motor, and is configured to rotate the circular disk body 133 to an arbitrary rotational phase.

The circular disk body 133 is provided with an inclined step part 133A at an intermediate position between the outer circumferential portion and the inner circumferential portion so that they can be shifted in the axis direction. This circular disk body 133 is made of a metal material, and is subjected to surface processing so as to easily reflect light.

The circular disk body 133 is provided with, at a position on the side that faces away from the support base 79, a circular holding member 136 that rotates together with the circular disk body 133. The holding member 136 is provided with a circular upper surface part 136A, and a tubular circumferential surface part 136B that extends to one side in the axis direction from the outer circumferential portion of the upper surface part 136A. This holding member 136 is provided so as to cover the inner circumferential part of the circular disk body 133. The circular disk body 133 and the holding member 136 are coupled with bolts at four positions that are distanced from each other in the circumferential direction, so that no gap is generated between the abutting positions. Thus, the circular disk body 133 and the holding member 136 are provided so as to be rotatable together.

The circular disk body 133 has a measurement through hole 137 through which light from grain received by the light-receiving part 59 passes, at a position that corresponds to the cut-out recess 134 and is located inward in the radial direction thereof. The upper surface part 136A of the holding member 136 is provided with, at a position that corresponds to the measurement through hole 137 of the circular disk body 133, an insertion hole 138 through which light from grain is transmitted when the circular disk body 133 is located at the measurement rotational position. The configuration is such that light from grain passes through the light-receiving opening 123 of the support base 79, the measurement through hole 137 of the circular disk body 133, and the insertion hole 138 of the holding member 136, and enters a light entrance part 139 of the spectroscopic analysis part 120.

Furthermore, the holding member 136 is provided with a correction optical filter through which light from the halogen lamp 50 is transmitted to enter the spectroscopic analysis part 120. This optical filter functions as a correction mechanism 200 that takes in the light from the halogen lamp 50, and obtains light information for correction, which is to be used in correcting an evaluation result regarding the grain.

Figure 17:
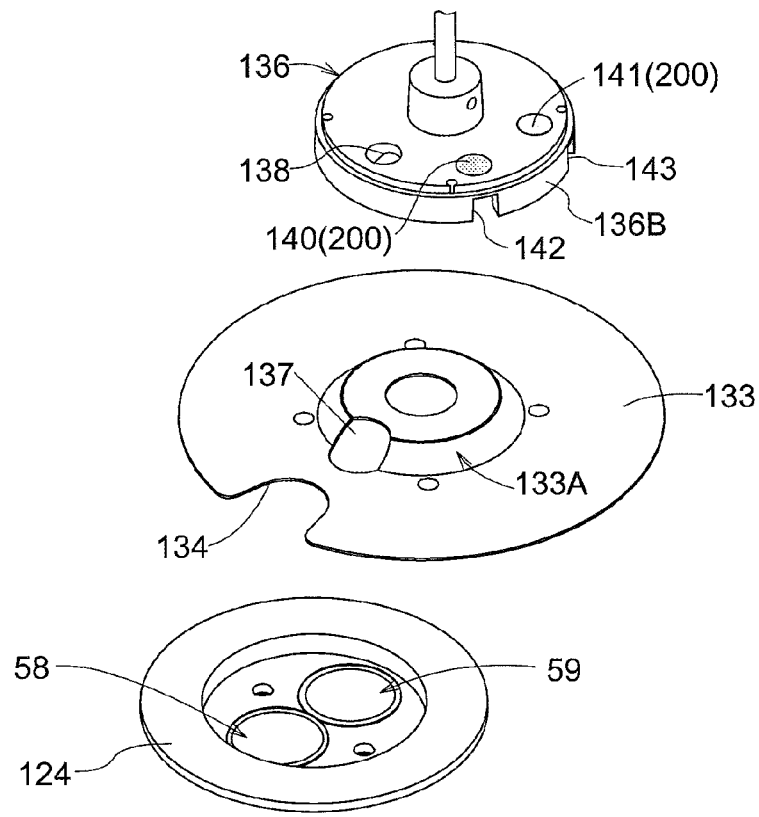
FIG. 17 is an exploded perspective view of main parts of the spectroscopic measurement unit performing the measurement processing.

As shown in FIG. 17, the holding member 136 is provided with a reference filter 140 and a wavelength correction filter 141 that serve as correction optical filters, at positions that have the same distance from the rotation center in the radial direction, and are different from each other in the circumferential direction. They are provided at positions that correspond to the step part 133A of the circular disk body 133. The holding member 136 is further provided with, in the circumferential part thereof, cut-outs 142 and 143. The cut-outs 142 and 143 are located at positions on the outer side in the radial direction of the mounted reference filter 140 and the wavelength correction filter 141, and penetrate the circumferential part in the radial direction.

The arrangement of the lamp housing 70 and the holding member 136 is such that, when the circular disk body 133 is rotated so that the cut-out 142 or 143 formed in the circumferential surface part 136B of the holding member 136 is located at the position that correspond to the slit 81 of the lamp housing 70, light that is projected via the slit 81 to the outside can pass through the cut-out 142 or 143 to reach the step part 133A of the circular disk body 133.

Figure 19:
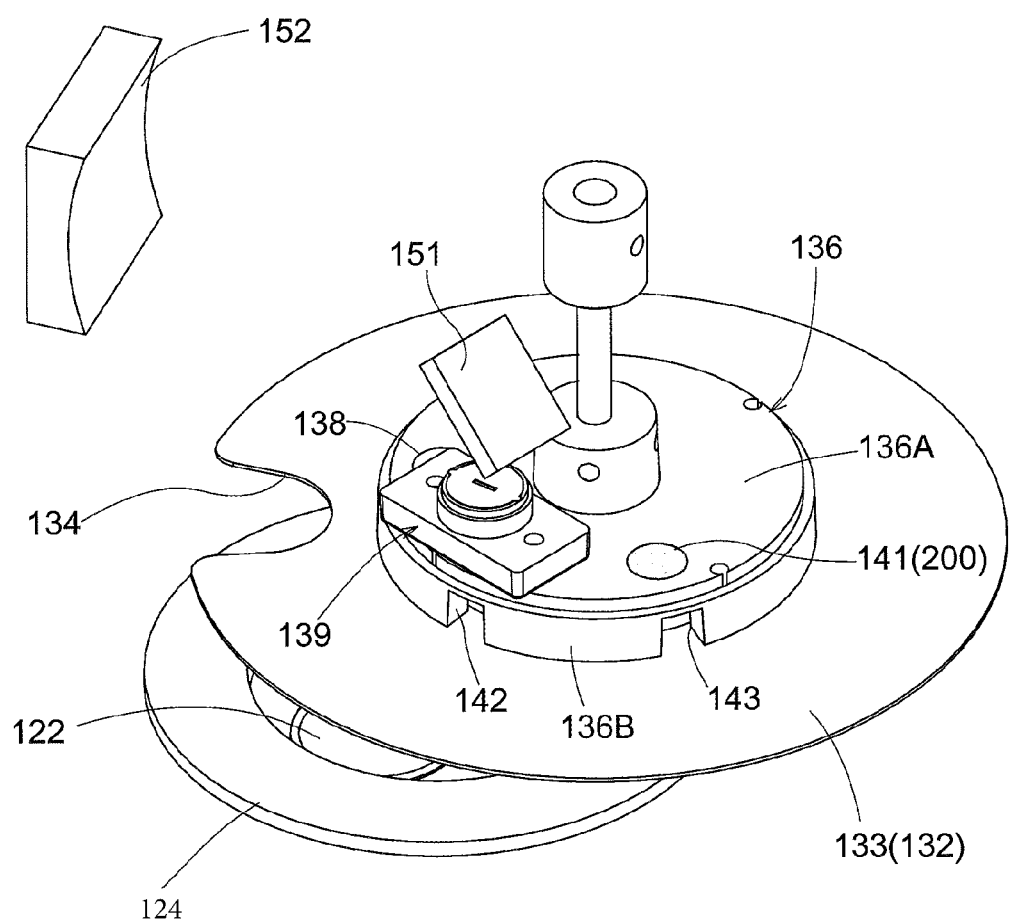
FIG. 19 is a perspective view of the main parts of the spectroscopic measurement unit performing light amount correction processing.
Figure 20:
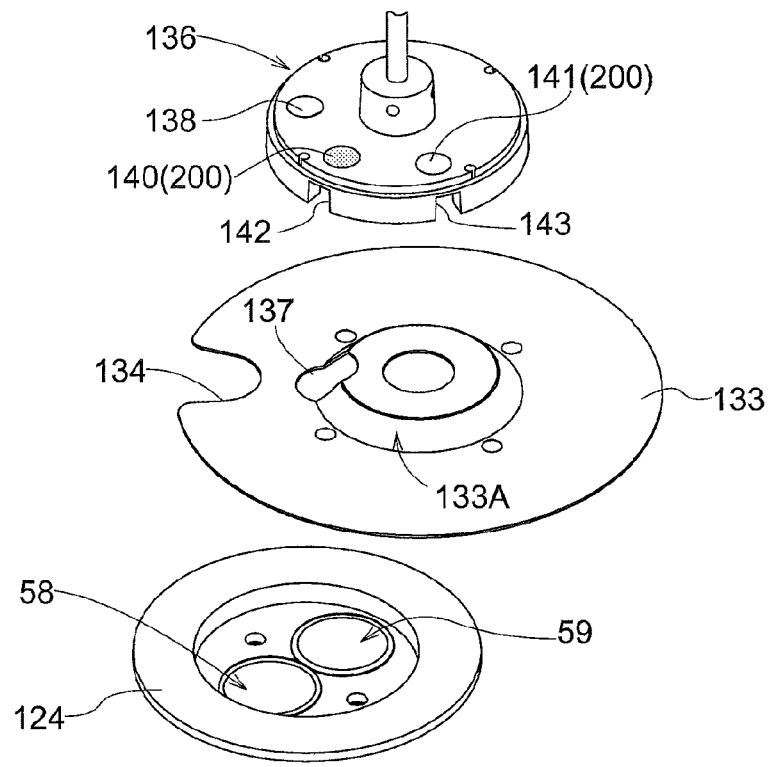
FIG. 20 is an exploded perspective view of the main parts of the spectroscopic measurement unit performing the light amount correction processing.

In other words, as shown in FIGS. 19 to 21, when the circular disk body 133 is displaced from the measurement rotational position, and is located at a reference rotational position, the cut-out 142 that corresponds to the reference filter 140 is located to correspond to the slit 81 formed in the lamp housing 70. The configuration is such that light that was projected and has passed through the cut-out 142 is reflected off the inclined surface of the step part 133A of the circular disk body 133, and enters the light entrance part 139 of the spectroscopic analysis part 120 through the reference filter 140.

Furthermore, although not shown, when the circular disk body 133 is displaced from the measurement rotational position, and is located at a wavelength correction (calibration) rotational position, the cut-out 143 that corresponds to the wavelength correction filter 141 is located to correspond to the slit 81 formed in the lamp housing 70. The configuration is such that light that was projected and has passed through the cut-out 143 is reflected off the inclined surface of the step part 133A of the circular disk body 133, and enters the light entrance part 139 of the spectroscopic analysis part 120 through the wavelength correction filter 141.

Accordingly, the circular disk body 133 is configured to also serve as a light reflector that reflects light from the halogen lamp 50 and guides the reflected light to the reference filter 140 and the wavelength correction filter 141, when the shutter 132 is in the closed state.

Although not shown, a standby position is set at the position at which none of the measurement through hole 137 of the circular disk body 133, the reference filter 140, and the wavelength correction filter 141 corresponds to the light entrance part 139. When the circular disk body 133 is located at the standby position, the shielding portion of the circular disk body 133 is located at the position that corresponds to the light entrance part 139 of the spectroscopic analysis part 120. Thus, the state is obtained in which light from the halogen lamp 50 is prevented from passing through the light-projecting part 58, and is not supplied to the reference filter 140 and the wavelength correction filter 141.

The circular disk body 133 is configured to be able to be operated, with the action of the driving motor 135, to the standby position, the measurement rotational position, the wavelength correction rotational position, or the reference rotational position. The driving motor 135 is coupled to the circular disk body 133 via the holding member 136. A drive shaft 135a of the driving motor 135 is directly coupled to the holding member 136 without a gear interposed therebetween, so that no phase error due to backlash occurs.

Accordingly, the circular disk body 133, the holding member 136, the driving motor 135 and the like constitute the switching mechanism 121. Furthermore, the shutter 132 and the correction mechanism 200 (the reference filter 140 and the wavelength correction filter 141) are provided so as to be lined up on the same plane, and to be movable together so that they switch between a state in which the shutter 132 operates, and a state in which the correction mechanism 200 (reference filter 140 and the wavelength correction filter 141) operates. Note that the shutter 132, the reference filter 140 and the wavelength correction filter 141 are slightly shifted in the axis direction, but "the same plane" in this context includes such a state in which they are slightly shifted from each other.

A spectroscopic analysis method is a known technique, and thus details thereof will not be described. But, the configuration of the spectroscopic analysis part 120 will be briefly described.

Figure 13:
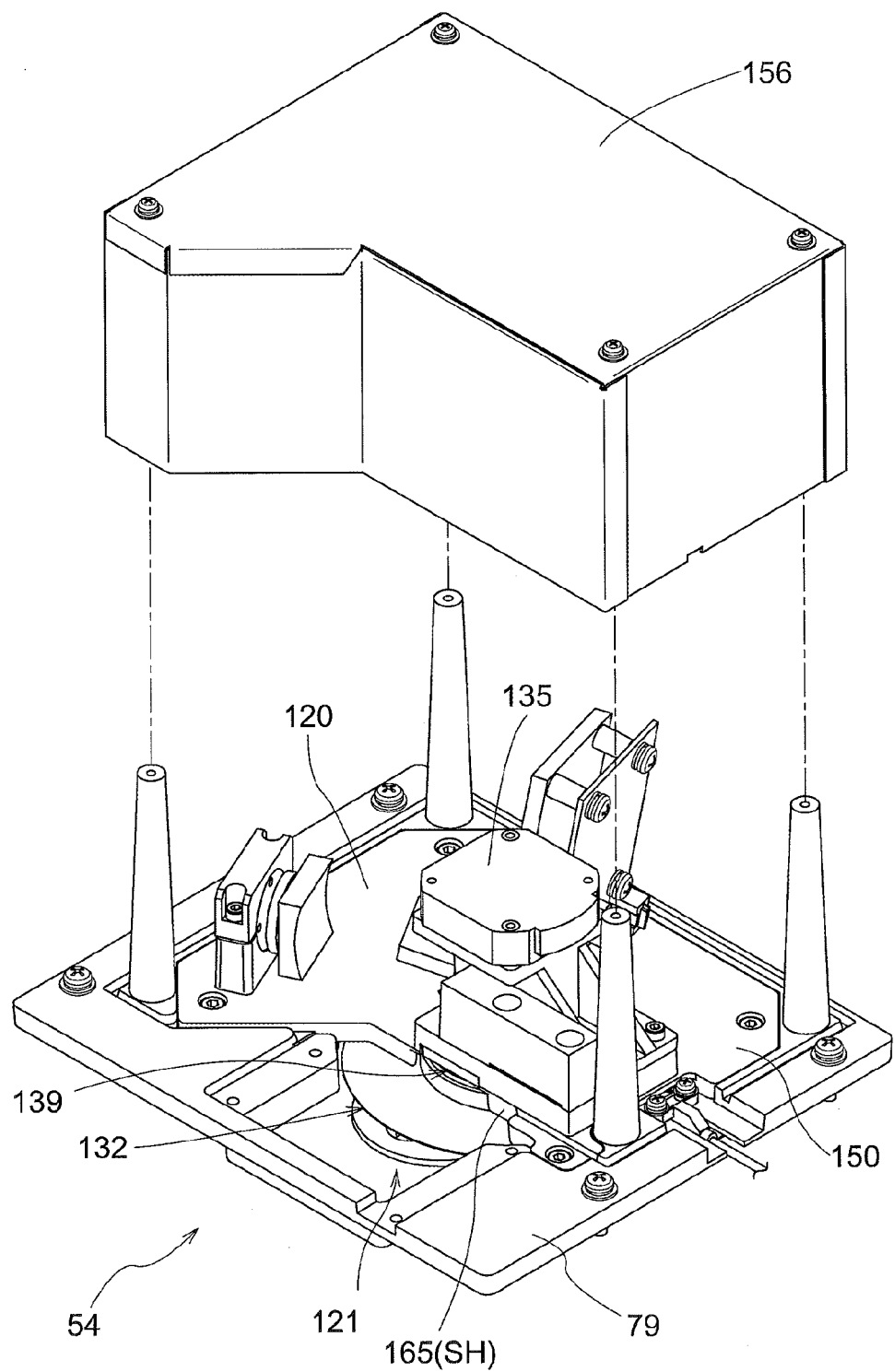
FIG. 13 is a perspective view of a spectroscopic measurement unit with a spectroscopic unit cover removed.

As shown in FIGS. 13 and 14, the spectroscopic analysis part 120 is provided with, for example: a base member 150; the above-described light entrance part 139 on which, for example, light for measurement is incident; a reflecting mirror 151 that reflects the light incident on the light entrance part 139 in a direction that is substantially orthogonal to the incident direction; a diffraction grating 152 that is concave-shaped and disperses the light reflected by the reflecting mirror 151 into rays of light with different wavelengths; a sensor unit 155 in which an NMOS-type light-receiving sensor 153 with 128 channels for receiving the dispersed rays of light, and an electric circuit part 154 that converts information of the detected light into digital signals are provided integrally with each other; the driving motor 135 that drives to rotate the circular disk body 133; and a spectroscopic unit cover 156 that covers the entire spectroscopic analysis part with the base member 150 serving as a bottom plate.

The light entrance part 139 is mounted while being inserted into a recess 150a formed in the base member 150. The reflecting mirror 151 is supported by a supporting bracket 151a that is fixed to the base member 150. The diffraction grating 152 is supported by a supporting bracket 157 that is fixed to the base member 150. Furthermore, the driving motor 135 is supported by a motor supporting bracket 158 that is fixed to the base member 150. In this way, the components are fixed to the base member 150, and the base member 150 is fixed to the support base 79 with bolts at a plurality of positions, so that the components are not displaced due to vibration of the machine body, or the like.

The light entrance part 139 is provided with, for example, a sharp-cut filter 160 through which only light with a wavelength longer than a predetermined wavelength is transmitted, and a slit forming body 162 in which a light-projecting slit 161 is formed in a state in which they are held by a filter holder 159.

An optical location sensor 164 that detects the circular disk body 133 reaching the standby position is provided at a position below the motor supporting bracket 158 that supports the driving motor 135, the optical location sensor 164 being fixed to the base member 150. This location sensor 164 is configured to detect an end edge of the cut-out recess 134. In other words, the circular disk body 133 is driven, by the driving motor 135, to rotate to the standby position in a predetermined direction, and is stopped at the position when the location sensor 164 has detected a predetermined end edge of the cut-out recess 134. The circular disk body 133 is therefore always driven in the same rotational direction.

The spectroscopic unit cover 156 has the peripheral wall that extends along the outer peripheral edge of the base member 150, and has a shape such that its front surface on the upper side is covered by the upper wall. Thus, the spectroscopic unit cover 156 is configured to perform shielding to prevent the entrance of light from the outside. In this spectroscopic analysis part 120, light enters the light entrance part 139, and is dispersed by the diffraction grating 152, and the light-receiving sensor 153 detects, for the respective channels, the amounts of the light at different wavelengths. The electric circuit part 154 transmits, to the control unit 55, an output signal obtained by converting a received light signal for each channel into a 16-bit digital signal.

In the above-described configuration, a shielding part SH is provided that separates an area between the halogen lamp 50 and the light-projecting part 58 from an area between the light-receiving part 59 and the light entrance part 139 of the spectroscopic measurement unit 54, and prevents light from the light-projecting part 58 from directly entering the light-receiving part 59. Moreover, the area between the halogen lamp 50 and the light-projecting part 58, and the area between the light-receiving part 59 and the light entrance part 139 of the spectroscopic measurement unit 54 are configured, over the entirety thereof, as air transmission areas in which light is transmitted through air, without a light transmission member.

More specifically, as shown in FIG. 18, the lamp housing 70 covers the periphery of the halogen lamp 50, and prevents the spectroscopic measurement unit 54 side from being irradiated with light from the halogen lamp 50. Furthermore, the holding member 136 is configured to separate the area between the cut-out recess 134 and the measurement through hole 137 of the circular disk body 133. As a result, even when the circular disk body 133 is located at the measurement rotational position, light from the halogen lamp 50 that passes through the cut-out recess 134 is prevented from being supplied to the light entrance part 139 of the spectroscopic measurement unit 54 via the measurement through hole 137.

The holding member 136 is provided with the two cut-outs 142 and 143 through which reference light and wavelength correction light are inserted, but light from the halogen lamp 50 is prevented from being supplied to the light entrance part 139 of the spectroscopic measurement unit 54 via these cut-outs 142 and 143.

In other words, as shown in FIG. 13, a covering part 165 is formed at the position at which the light entrance part 139 of the base member 150 is provided. In a state in which the holding member 136 is attached, the covering part 165 opens a portion of the holding member 136 that faces the lamp housing 70 and covers the remaining portion. Thus, the covering part 165 prevents the supply of light from the halogen lamp 50 to the light entrance part 139 of the spectroscopic measurement unit 54 via the cut-out 142 or 143.

In this way, the area between the halogen lamp 50 and the light-projecting part 58 and the area between the light-receiving part 59 and the light entrance part 139 of the spectroscopic measurement unit 54 are separated from each other.

Furthermore, as described above, the protruding ridge 130 that protrudes to the outside (to the grain side) is provided between the light-projecting part 58 and the light-receiving part 59 so as to prevent light from the light-projecting part 58 from directly entering the light-receiving part 59, and the shielding peripheral wall 131 that encloses the light-projecting part 58 and the light-receiving part 59 is provided so as to prevent the entrance of light from the environment. In this way, light from the light-projecting part 58 is prevented from directly entering the light-receiving part 59.

Accordingly, the shielding part SH is constituted by the lamp housing 70, the holding member 136, the covering part 165 of the base member 150, the protruding ridge 130, the shielding peripheral wall 131 and the like.

As shown in FIG. 18, when the circular disk body 133 is located at the measurement rotational position, the area between the halogen lamp 50 and the light-projecting part 58, and the area between the light-receiving part 59 and the light entrance part 139 of the spectroscopic measurement unit 54 are configured as air transmission areas in which light is transmitted through air, without including a light transmission member. As is clear from the drawing, the configuration is such that the halogen lamp 50 and the light-projecting part 58 are arranged linearly, and light projected from the halogen lamp 50 is directly guided to the light-projecting part 58. In other words, the configuration is such that light projected from the halogen lamp 50 is linearly guided to the light-projecting part 58 without a light refracting member such as a light reflector or an optical fiber being interposed between the halogen lamp 50 and the light-projecting part 58.

Operation of Control Unit

The control operation of the control unit 55 will be described.

When performing measurement processing, the control unit 55 controls the operation in the following manner:

Each time a set time has elapsed, the control unit 55 controls the operations of the driving motor 135 and the spectroscopic analysis part 120 to perform wavelength correction (calibration) processing and light amount correction processing.

In the wavelength correction processing, the circular disk body 133 is moved from the standby position to the wavelength correction rotational position through the measurement rotational position, a result of measurement by the light-receiving sensor 153 at this time is compared with reference data measured in advance, and it is checked whether or not there is a variation in the wavelengths measured by light receiving elements of the 128 channels. If there is a variation in the wavelengths, the wavelength correction processing is executed in an appropriate state.

Then, the circular disk body 133 is moved to the reference rotational position, and the light amount correction processing is executed. In other words, a result of measurement by the light-receiving sensor 153 at this time is compared with initial data measured in advance, it is determined whether or not the halogen lamp 50 has deteriorated, and a correction coefficient for the measured data is obtained. The result of measurement by the light-receiving sensor 153 is corrected based on this correction coefficient.

After the light amount correction processing has been executed, the circular disk body 133 is returned to the standby position, and stands by until the set time elapses. Thus, such wavelength correction processing and reference processing are repeatedly executed each time the set time has elapsed. Furthermore, when grain is stored in the sampling unit 25 during a reaping operation, and the full capacity sensor 28 has detected the full capacity state in which the sampling unit 25 is full with grain, measurement of the stored grain is executed as a result of interrupt processing. In other words, the circular disk body 133 is rotated to the measurement rotational position, and light from the halogen lamp 50 is projected to the grain stored in the sampling unit 25 through the light-projecting part 58. Light from the grain that is received by the light-receiving part 59 enters the spectroscopic analysis part 120, and the light-receiving sensor 153 measures spectroscopic spectral data indicating the intensities of the light with different wavelengths. A well-known spectroscopic analysis method is used to calculate, based on the measurement results, the amounts of components of the grain such as moisture content and protein by using arithmetic processing. The obtained result is displayed on the display device 20 of the operation unit 7.

Other Embodiments (1) The foregoing embodiment has described a configuration in which the shutter 132 and the correction mechanism 200 (the reference filter and the wavelength correction filter) are located on the same plane, and are provided integrally with the circular disk body 133, which serves as a rotation body that rotates about an axis that is orthogonal to the mounting surface on which the light-projecting part 58 and the light-receiving part 59 are mounted, and, by rotation of the circular disk body 133, switching is performed between the measurement state in which the shutter 132 is in the open state, and the correction state in which the correction mechanism 200 operates. But, instead of such a configuration, the following configurations (1-1) to (1-3) may be used.

Configuration (1-1): the shutter 132 and the correction mechanism 200 are arranged being largely shifted in the rotation axis direction.

Configuration (1-2): the shutter 132 and the correction mechanism 200 are provided on a moving body that slides and moves linearly.

Configuration (1-3): the shutter 132 and the correction mechanism 200 are respectively mounted on separate moving operation bodies.

(2) In the foregoing embodiment, the shutter 132 is configured to also serve as a light reflector, but the shutter 132 and the light reflector may be provided separately.

(3) The foregoing embodiment has described a configuration in which the light source (halogen lamp 50) and the light-projecting part 58 are arranged linearly, but a reflecting mirror may be provided between the light source and the light-projecting part 58.

(4) The foregoing embodiment has described a configuration in which the ventilation casing is configured by the lamp housing 70 and a separate discharge duct, but the ventilation casing may be configured by a single case in which a light source and a fan are provided integrally therewith.

(5) The foregoing embodiment has described a configuration in which the optical grain evaluation device 19 is provided on the outer side of the grain tank 5 while being located on the operation unit 7 side of the front side wall 5F of the grain tank 5, but, instead of such a configuration, a configuration is also possible in which the optical grain evaluation device 19 is provided in a space obtained by forming a recess inward in the front side wall 5F of the grain tank 5.

Figure 23:
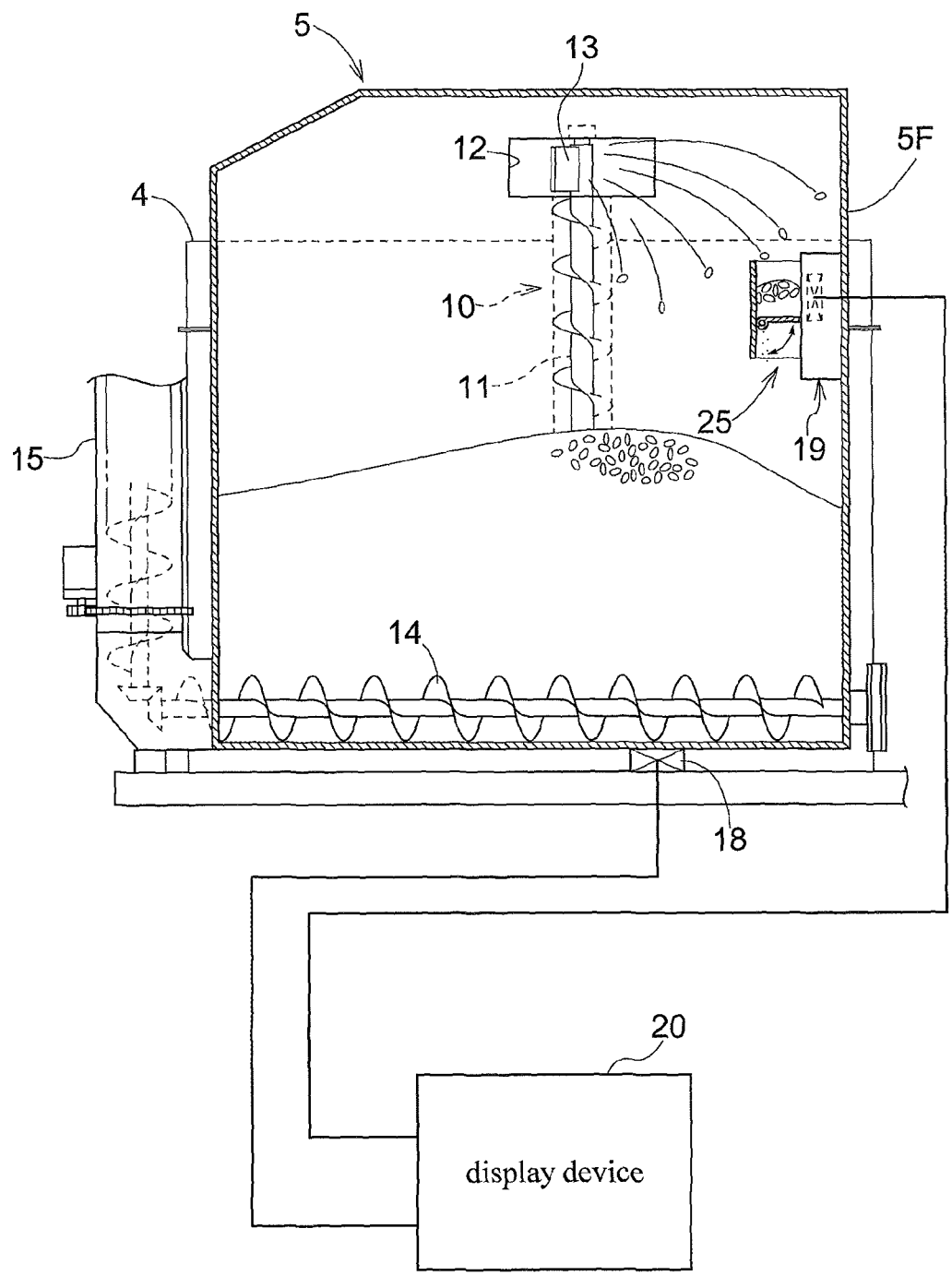
FIG. 23 is a side view in vertical section of a grain tank illustrating a state in which an optical grain evaluation device is installed, according to a modified embodiment.
Figure 24:
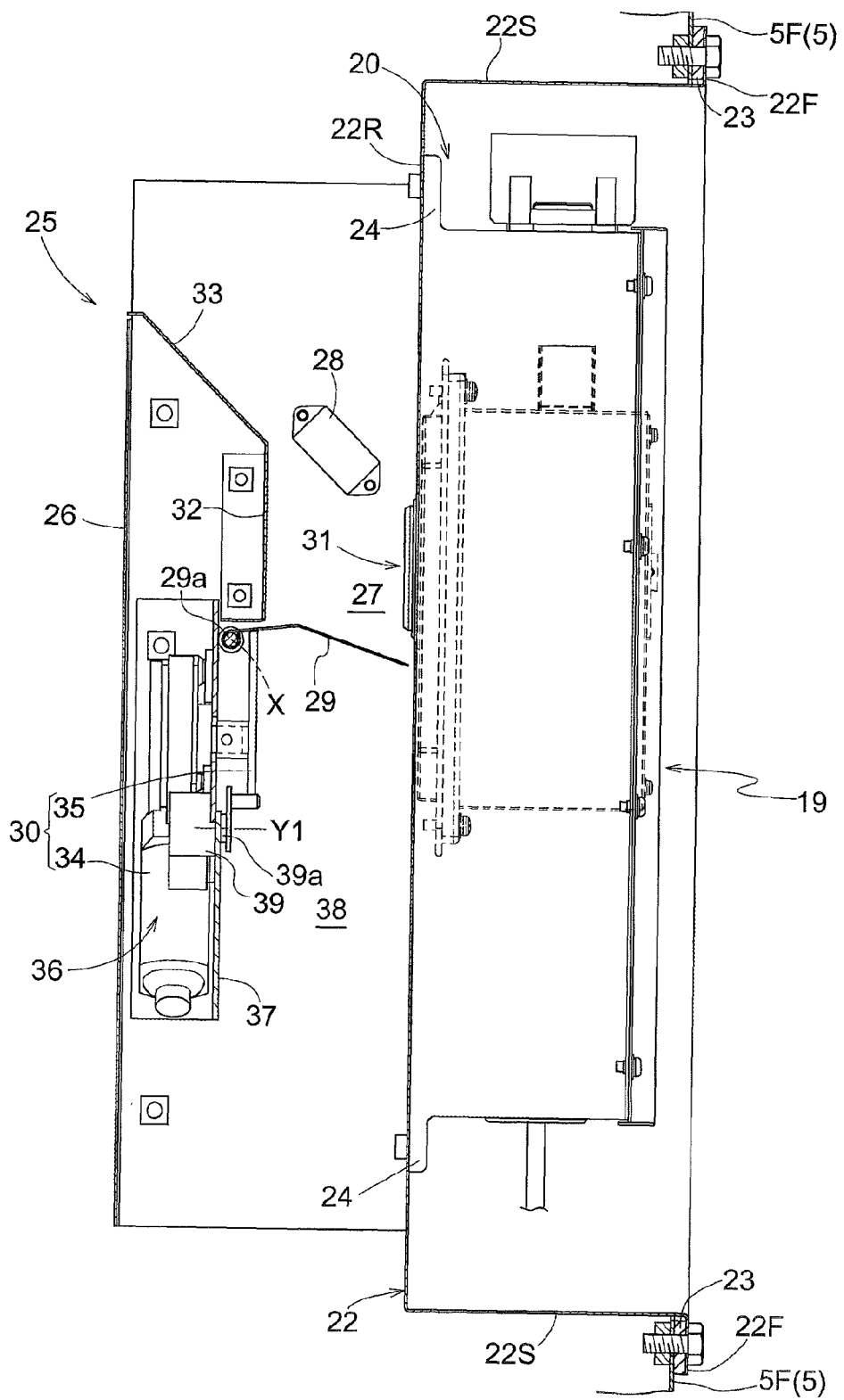
FIG. 24 is a side view in vertical section of a sampling unit and the optical grain evaluation device of the modified embodiment.

In other words, the configuration is such that, as shown in FIGS. 23 and 24, as a result of a measurement room forming body 22 being fitted into and mounted in an attachment opening formed in the front side wall 5F, a space is formed by a recess in the grain tank 5, and the optical grain evaluation device 19 is provided in this space formed by the measurement room forming body 22.

The measurement room forming body 22 is provided with: a rear wall 22R that is located inward of the grain tank 5 compared to the front side wall 5F of the grain tank 5; and a peripheral wall 22S that protrudes forward from the entire peripheral portion of the rear wall 22R toward the grain tank 5 and reaches the front side wall 5F. The measurement room forming body 22 is, as a whole, box-shaped.

The measurement room forming body 22 is mounted from the front side of the travelling machine body, and is fixed to the grain tank 5 by a connection flange 22F provided over the entire periphery of the peripheral wall 22S being connected to the front surface side of the front side wall 5F with connection bolts. An anti-vibration rubber 23 (see FIG. 24) for suppressing vibration transmission to the optical grain evaluation device 19 is interposed between the connection flange 22F of the measurement room forming body 22 and the front side wall 5F of the grain tank 5. The anti-vibration rubber 23 is provided over the entire periphery.

The anti-vibration rubber 23 has a sealing function of sealing the measurement room forming body 22 to the front side wall 5F.

The optical grain evaluation device 19 is coupled, using the coupling flange parts 24 on both the upper and lower sides thereof, to the rear wall 22R of the measurement room forming body 22 with bolts. Accordingly, the optical grain evaluation device 19 is located inward of the grain tank 5 compared to the front side wall 5F of the grain tank 5, while being housed in a space separated from the grain storage space 5b of the grain tank 5. In this configuration, dust is not likely to attach to the outer surface of the optical grain evaluation device 19.

(6) The foregoing embodiment has described a configuration in which the optical grain evaluation device is mounted on a head-feeding type combine harvester, but, instead of this, the optical grain evaluation device may be mounted on a normal-type combine harvester that is configured to load the entirety of reaped grain culms from the grain roots to the ear tips in a threshing chamber. Furthermore, the optical grain evaluation device is not limited to one provided on a combine harvester, and may be provided on, for example, a grain drier that performs drying processing on harvested grain, a storage facility in which grain is stored for extended periods of time, or the like.

If the optical grain evaluation device is provided on a grain drier, there may be cases where the optical grain evaluation device is mounted on an inclined guide surface on which grain is guided to flow downward. In this configuration, a flat-shaped measuring head that does not protrude to a region in which grain is present is preferably used so as not to get in the way of grain flow. In other words, instead of the protruding cover member 124 according to the embodiment, the light-projecting glass plate 126 and the light-receiving glass plate 127 are provided in a flat state facing the region in which grain is present.

INDUSTRIAL APPLICABILITY

The present invention is applicable to an optical grain evaluation device that evaluates components contained in grain such as rice and wheat, using optical measurement.

DESCRIPTION OF REFERENCE SIGNS

50 Light source
58 Light-projecting part
59 Light-receiving part
60 Grain evaluation unit
87 Cooling fan
90 Air supply port
93 Air discharge port
94 Ventilation casing
132 Shutter
133 Rotation body
200 Correction mechanism
SH Shielding part

What is claimed is:
1. An optical grain evaluation device comprising:
a light source;
a light-projecting part through which light from the light source is projected to stored grain;
a light-receiving part on which light that has been projected to the grain through the light-projecting part and transmitted through the grain is incident, the light-receiving part being lined up with the light-projecting part at a distance;
a grain evaluation unit configured to evaluate the grain based on information relating to the light received by the light-receiving part;
a shielding part that separates an area between the light source and the light-projecting part from an area between the light-receiving part and the grain evaluation unit, so as to prevent light from the light-projecting part from directly entering the light-receiving part; and
a shutter that is provided separate from the shielding part so as to be switchable between an open state in which the light from the light source is allowed to pass through the light-projecting part, and a closed state in which the light is prevented from passing through the light-projecting part,
wherein the area between the light source and the light-projecting part, and the area between the light-receiving part and the grain evaluation unit are configured, over the entirety of the areas, as air transmission areas in which light is transmitted through air.
2. The optical grain evaluation device according to claim 1, wherein the light source and the light-projecting part are arranged linearly.

3. The optical grain evaluation device according to claim 1, further comprising:
a correction mechanism configured to take in the light from the light source and obtain light information for correction for use in correcting an evaluation result regarding the grain when the shutter is in the closed state,
wherein the shutter and the correction mechanism are provided as one piece.

4. The optical grain evaluation device according to claim 3, wherein the correction mechanism is provided with a correction optical filter through which the light from the light source passes to enter the grain evaluation unit.

5. The optical grain evaluation device according to claim 3, further comprising:
a light reflector configured to reflect the light from the light source and guide the light to the correction mechanism when the shutter is in the closed state.

6. The optical grain evaluation device according to claim 5, wherein the shutter is also used as the light reflector.

7. The optical grain evaluation device according to claim 3, wherein the shutter and the correction mechanism are lined up on the same plane, and are provided so as to be movable together to switch between a state in which the shutter operates, and a state in which the correction mechanism operates.

8. The optical grain evaluation device according to claim 7,
wherein the shutter and the correction mechanism are provided integrally with a rotation body that rotates about an axis that is orthogonal to a mounting surface on which the light-projecting part and the light-receiving part are mounted, and
the optical grain evaluation device is configured to be switched between a measurement state in which the shutter is in the open state, and a correction state in which the correction mechanism operates, by rotating the rotation body.

9. The optical grain evaluation device according to claim 1, further comprising:
a cooling fan configured to generate cooling air for cooling the light source; and
a ventilation casing in which the light source and the cooling fan are arranged, and through which the cooling air is passed,
wherein the ventilation casing is formed such that an air supply port for supplying the cooling air and an air discharge port for discharging the cooling air to the outside are located on the same plane.

10. A combine harvester provided with the optical grain evaluation device according to claim 1.

* * * * *